(12) United States Patent
Seger et al.

(10) Patent No.: US 12,286,439 B2
(45) Date of Patent: Apr. 29, 2025

(54) INHIBITORS OF ERK NUCLEAR TRANSLOCATION

(71) Applicants: Yeda Research and Development Co. Ltd., Rehovot (IL); Universitat de Barcelona, Barcelona (ES); Institució Catalana de Recerca I Estudis Avançats, Barcelona (ES)

(72) Inventors: Rony Seger, Rehovot (IL); Karen Flores, Rehovot (IL); Xavier Barril Alonso, Barcelona (ES); Carlos Galdeano Cantador, Barcelona (ES)

(73) Assignees: Yeda Research and Development Co. Ltd., Rehovot (IL); Universitat de Barcelona, Barcelona (ES); Institució Catalana de Recerca I Estudis Avançats, Barcelona (ES)

( * ) Notice: Subject to any disclaimer, the term of this patent is extended or adjusted under 35 U.S.C. 154(b) by 800 days.

(21) Appl. No.: 17/337,570

(22) Filed: Jun. 3, 2021

(65) Prior Publication Data

US 2021/0292338 A1 Sep. 23, 2021

Related U.S. Application Data

(63) Continuation of application No. PCT/IL2019/051326, filed on Dec. 3, 2019.

(60) Provisional application No. 62/774,360, filed on Dec. 3, 2018.

(51) Int. Cl.
C07D 498/04 (2006.01)
A61K 45/06 (2006.01)
A61P 35/00 (2006.01)

(52) U.S. Cl.
CPC ............ *C07D 498/04* (2013.01); *A61K 45/06* (2013.01); *A61P 35/00* (2018.01)

(58) Field of Classification Search
CPC .................................................. C07D 498/04
See application file for complete search history.

(56) References Cited

U.S. PATENT DOCUMENTS

2014/0179743 A1 6/2014 Shapiro et al.

FOREIGN PATENT DOCUMENTS

EP 3046929 7/2016
WO WO 2020/115744 6/2020

OTHER PUBLICATIONS

STN Reg. No. 631864/85/2, entered into STN Dec. 29, 2003, p. 1. (Year: 2003).*

International Preliminary Report on Patentability Dated Jun. 17, 2021 From the International Bureau of WIPO Re. Application No. PCT/IL2019/051326. (8 Pages).
International Search Report and the Written Opinion Dated Feb. 21, 2020 From the International Searching Authority Re. Application No. PCT/IL2019/051326. (16 Pages).
Ananthan et al. "High Throughput Screening for Inhibitors of Mycobacterium Tuberculosis H37Rv", Tuberculosis, 89(5): 334-353, Sep. 2009.
Arafeh et al. "Combined Inhibition of MEK and Nuclear ERK Translocation Has Synergisitic Antitumor Activity in Melanoma Cells", Scientific Reports, 7(1): 16345-1-16345-9, Published Online Nov. 27, 2017.
Birkner et al. "The Role of ERK Signaling in Experimental Autoimmune Encephalomyelitis", International Journal of Molecular Sciences, 18(9): 190-1-190-14, Published Online Sep. 15, 2017.
Bryant et al. "KRAS: Feeding Pancreatic Cancer Proliferation", Trends in Biochemical Sciences, 39(2): 91-100, Feb. 2014.
Campbell et al. "K-Ras Promotes Growth Transformation and Invasion of Immortalized Human Pancreatic Cells by Raf and Phosphatidylinositol 3-Kinase Signaling", Cancer Research, 67(5): 2098-2106, Mar. 1, 2007.
Deer et al. "Phenotype and Genotype of Pancreatic Cancer Cell Lines", Pancreas, 39(4): 425-435, May 2010.
Defaux et al. "Discovery of (7-Aryl-1,5-Naphthyridin-2-Y1)Ureas as Dual Inhibitors of ERK2 and Aurora B Kinases With Antiproliferative Activity Against Cancer Cells", Bioorganic & Medicinal Chemstry Letters, XP029041743, 24(16): 3748-3752, Available Online Jul. 3, 2014.

(Continued)

*Primary Examiner* — Kamal A Saeed
*Assistant Examiner* — Karen Cheng

(57) ABSTRACT

Described herein are compounds having Formula I or Formula II:

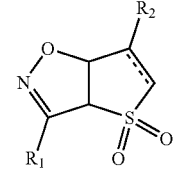

Formula I

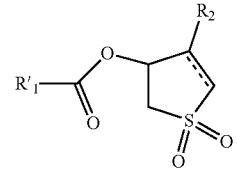

Formula II wherein each dashed line independently represents a saturated or unsaturated bond; $R_1$ and $R'_1$ are aryl or heteroaryl as defined herein; and $R_2$ and $R'_2$ are as defined herein. Further described is a method of inhibiting nuclear translocation of ERK1/2 in a cell, by contacting the cell with a compound having Formula I or Formula II. The compounds may also be for use in treating a disease or disorder associated with nuclear translocation of ERK1/2.

8 Claims, 20 Drawing Sheets
(3 of 20 Drawing Sheet(s) Filed in Color)
Specification includes a Sequence Listing.

(56) References Cited

OTHER PUBLICATIONS

Flores et al. "Stimulated Nuclear Import by Beta-Like Importins", F1000Prime Reports, 5(41): 1-7, Published Online Oct. 1, 2013.
Glowienke et al. "Structure-Activity Considerations and In Vitro Approaches to Assess the Genotoxicity of 19 Methane-, Benzene- and Toluenesulfonic Acid Esters", Mutation Research, 581(1-2): 23-34, Available Online Dec. 21, 2004.
Lukevics et al. "Cytotoxic Activity of Silyl-and Germyl-Substituted 4,4-Dioxo-3a,6a-Dihydrothieno[2,3-d]Isoxaz Olines-2", Metal-Based Drugs, XP055666916, 7(2): 63-66, Jan. 2000.
Marinone Albini et al. "Selectivity in Cycloadditions—X: Regiochemistry of Cycloadditions of Nitrile Oxides to Thiopene and Benzothiopene 1, 1-Dioxides", Tetrahedron, 38(24): 3629-3639, Jan. 1982.
Mebratu et al. "How ERK1/2 Activation Controls Cell Proliferation and Cell Death Is Subcellular Localization the Answer?", Cell Cycle, XP055331432, 8(8): 1168-1175, Published Online Apr. 15, 2009.
Michailovici et al. "Nuclear to Cytoplasmic Shuttling of ERK Promotes Differentiation of Muscle Stem/Progenitor Cells", Development, 141(13): 2611-2620, Jul. 2014.
Plotnikov et al. "Nuclear Extracellular Signal-Regulated Kinase 1 and 2 Translocation Is Mediated by Casein Kinase 2 and Accelerated by Autophosphorylation", Molecular and Cellular Biology, 31(17); 3515-3530, Sep. 2011.
Plotnikov et al. "The Nuclear Translocation of ERK1/2 as an Anticancer Target", Nature Communications, XP055331433, 6(Art. ID 6685): 1-11, Mar. 30, 2015.
Samadani et al. "Small-Molecule Inhibitors of ERK-Mediated Immediate Early Gene Expression and Proliferation of Melanoma Cells Expressing Mutated BRaf", Biochemistry Journal, XP055667183, 467(3): 425-438, May 1, 2015.
Schevzov et al. "Regulation of Cell Proliferation by ERK and Signal-Dependent Nuclear Translocation of ERK Is Dependent on Tm5NM1-Containing Actin Filaments", Molecular Biology of the Cell, MBoC, 26(13): 2475-2490, Jul. 1, 2015.
Varga et al. "A First-in-Human Phase I Study to Evaluate the ERK1/2 Inhibitor GDC-0994 in Patients With Advanced Solid Tumors", European Journal of Cancer, XP029843464, Oral Abstract, Session 2, 69(S11): # 18, Nov. 30, 2016.
Zehorai et al. "The Subcellular Localization of MEK and ERK—A Novel Nuclear Translocation Signal (NTS) Paves A Way to the Nucleus", Molecular and Cellular Endocrinology, XP026809642, 314(2): 213-220, Jan. 27, 2010.
Zhang et al. "Selective Killing of Cancer Cells by Small Molecules Targeting Heat Shock Stress Response", Biochemical and Biophysical Research Communications, XP029732579, 478(4): 1509-1514, Published Online Aug. 20, 2016.

\* cited by examiner

Z56

Z1: p-toluene analogue

Z2: ester analogue

Z3: sulfonamide + p-toluene analogue

A2185

DMSO | DMSO +TPA

D3 (1 μM) +TPA | D11 (1 μM) +TPA | D14 (1 μM) +TPA

INHIBITORS OF ERK NUCLEAR TRANSLOCATION

RELATED APPLICATIONS

This application is a Continuation Patent Application of PCT Application No. PCT/IL2019/051326 filed on Dec. 3, 2019 which claims the benefit of priority under 35 USC § 119(e) of U.S. Provisional Patent Application No. 62/774,360 filed on Dec. 3, 2018. The contents of the above applications are all incorporated by reference as if fully set forth herein in their entirety.

SEQUENCE LISTING STATEMENT

The ASCII file, entitled 87819Sequence Listing.txt, created on Jun. 3, 2021, comprising 1,264 bytes, submitted concurrently with the filing of this application is incorporated herein by reference.

FIELD AND BACKGROUND OF THE INVENTION

The present invention, in some embodiments thereof, relates to therapy, and more particularly, but not exclusively, to compounds that inhibit ERK1/2 nuclear translocation and to uses thereof in treating proliferative diseases and disorders such as cancer.

The ERK cascade plays a central role in the regulation of various cellular processes, including proliferation and differentiation. Therefore, its dysregulation is associated with diseases such as cancer. One of the hallmarks of the cascade is the nuclear translocation of ERK1/2, which is important mainly for the induction of proliferation, but less so for other ERK1/2-induced processes. The nuclear translocation of ERK1/2 is mediated by the phosphorylation of their nuclear translocation signal (NTS). This phosphorylation allows interaction of ERK1/2 with importin7, which carries ERK1/2 into the nucleus, where the ERK1/2 phosphorylates transcription factors.

Plotnikov et al. [*Nat Commun* 2015, 6:6685] describes an NTS-derived myristoylated phosphomimetic EPE (Glu-Pro-Glu) peptide which blocks the interaction of importin7 and ERK1/2, and consequently the nuclear translocation of ERK1/2.

Arafeh et al. [*Sci Rep* 2017, 7:16345] reports that the EPE peptide significantly reduced the viability of BRAF-mutant melanoma, as well as NRAS-mutant and NF1-mutant melanomas which are resistant to other ERK cascade inhibitors; and that EPE peptide exhibited synergy in combination with the MEK inhibitor trametinib in reducing the viability of NRAS-mutant melanomas.

Samadani et al. [*Biochem J* 2015, 467:425-438] describes compounds with a thienyl benzenesulfonate scaffold which were designed to inhibit ERK1/2 substrates containing an F-site or DEF motif. A crystallographic structure of 1,1-dioxo-2,3-dihydrothiophen-3-yl benzenesulfonate (also referred to therein as SF-3-026) bound to the inactive form of ERK2 was obtained and deposited in the PDB (Protein Data Bank) under accession code 3QYI. Analogs of SF-3-026 were prepared and compared with SF-3-026, and the naphthyl analog of SF-3-026 (SF-3-030) was reported to be the most potent inhibitor.

U.S. Patent Application Publication No. 2014/0179743, by some of the coauthors of Samadani et al. [*Biochem J* 2015, 467:425-438], describes non-ATP-dependent inhibitors of ERK which comprise a —S(=O)₂— linking group; and more particularly, compounds with a 1,1-dioxo-2,3-dihydrothiophen-3-yl or 1,1-dioxo-tetrahydrothiophen-3-yl moiety attached to a —O—S(=O)₂— or —N(R)—S(=O)₂— linking group, including SF-3-026 and SF-3-030.

Albini et al. [*Tetrahedron* 1982, 38:3629-3639] describes regioselective cycloaddition of thiophene-1,1-dioxide and 2,3-dihydrothiophene-1,1-dioxide to benzonitrile oxides.

Additional background art includes Ananthan et al. [Tuberculosis (Edinb) 2009, 89:334-353]; Birkner et al. [*Int J Mol Sci* 2017, 18:E1990]; Bryant et al. [*Trends Biochem Sci* 2014, 39:91-100]; Campbell et al. [*Cancer Res* 2007, 67:2098-2106]; Deer et al. [*Pancreas* 2010, 39:425-435]; Flores & Seger [*F1000Prime Rep* 2013, 5:41]; Glowienke et al. [*Mutat Res* 2005, 581:23-34]; Michailovici et al. [*Development* 2014, 141:2611-2620]; Plotnikov et al. [*Mol Cell Biol* 2011, 31:3515-3530]; and Schevzov et al. [*Mol Biol Cell* 2015, 26:2475-2490].

SUMMARY OF THE INVENTION

According to an aspect of some embodiments of the invention, there is provide a compound for use in treating a disease or disorder associated with nuclear translocation of ERK1/2, the compound being represented by Formula I or Formula II:

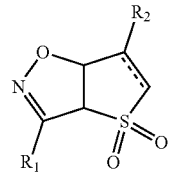

Formula I

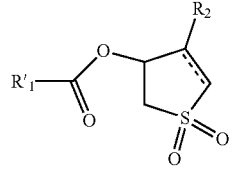

Formula II wherein:
each dashed line independently represents a saturated or unsaturated bond;
$R_1$ and $R'_1$ are each independently an aryl or heteroaryl, which is substituted or non-substituted; and
$R_2$ and $R'_2$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino,
wherein when $R_2$ is hydrogen, the dashed line in Formula I represents an unsaturated bond, and when $R'_2$ is hydrogen, the dashed line in Formula II represents an unsaturated bond.

According to an aspect of some embodiments of the invention, there is provide a compound represented by Formula I*:

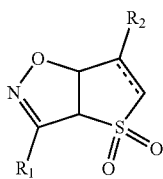

Formula I* wherein:
the dashed line represents a saturated or unsaturated bond;
$R_1$ is an aryl or heteroaryl, which is substituted or non-substituted; and
$R_2$ is selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino,
wherein when $R_2$ is hydrogen, the dashed line represents an unsaturated bond,
and wherein $R_1$ is not phenyl, 2,4,6-trimethylphenyl, 4-trifluoromethylphenyl, 4-chlorophenyl or 2,6-dichlorophenyl.

According to an aspect of some embodiments of the invention, there is provide a method of inhibiting nuclear translocation of ERK1/2 in a cell, the method comprising contacting the cell with a compound represented by Formula I or Formula II:

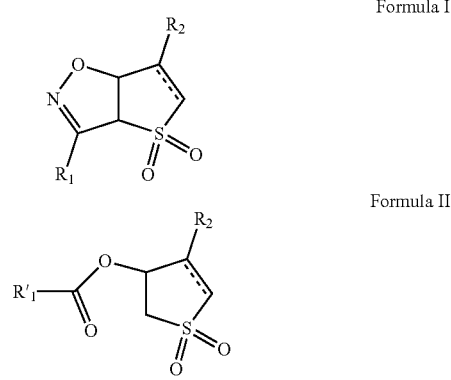

Formula I

Formula II wherein:
each dashed line independently represents a saturated or unsaturated bond;
$R_1$ and $R'_1$ are each independently an aryl or heteroaryl, which is substituted or non-substituted; and
$R_2$ and $R'_2$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino, wherein when $R_2$ is hydrogen, the dashed line in Formula I represents an unsaturated bond, and when $R'_2$ is hydrogen, the dashed line in Formula II represents an unsaturated bond, thereby inhibiting the nuclear translocation of ERK1/2.

According to some of any of the embodiments of the invention relating to Formulas I and II, the compound is represented by Formula I.

According to some of any of the embodiments of the invention relating to Formulas I and II, the compound is represented by Formula I.

According to some of any of the embodiments of the invention, the dashed line represents an unsaturated bond.

According to some of any of the respective embodiments of the invention, $R_2$ and/or $R'_2$ are hydrogen.

According to some of any of the respective embodiments of the invention, $R_2$ and/or $R'_2$ are each independently selected from the group consisting of hydrogen, halo and O-carboxy.

According to some of any of the respective embodiments of the invention, $R_1$ and/or $R'_1$ are each independently a substituted or non-substituted aryl or a substituted or non-substituted indolyl.

According to some of any of the respective embodiments of the invention, the indolyl is a substituted or non-substituted indol-3-yl.

According to some of any of the respective embodiments of the invention, the aryl or heteroaryl is substituted by one or more electron withdrawing groups.

According to some of any of the respective embodiments of the invention, the aryl or heteroaryl is substituted by at least two electron withdrawing groups.

According to some of any of the respective embodiments of the invention, the electron withdrawing groups are halo.

According to some of any of the respective embodiments of the invention, the halo is chloro.

According to some of any of the respective embodiments of the invention, $R_1$ and/or $R'_1$ are each independently phenyl.

According to some of any of the respective embodiments of the invention, $R_1$ and/or $R'_1$ are each independently a substituted phenyl.

According to some of any of the respective embodiments of the invention, the phenyl is substituted at a para position and/or a meta position thereof.

According to some of any of the respective embodiments of the invention, the phenyl is non-substituted at an ortho position thereof.

According to some of any of the respective embodiments of the invention, $R_1$ and/or $R'_1$ are each independently 3,4-dichlorophenyl or 3,5-dichlorophenyl.

According to some of any of the embodiments of the invention relating to a disease or disorder, the disease or disorder is a proliferative disease or disorder.

According to some of any of embodiments of the invention relating to a proliferative disease or disorder, the proliferative disease or disorder is cancer.

According to some of any of embodiments of the invention relating to cancer, the cancer is selected from the group consisting of breast cancer, cervical cancer, colorectal cancer, hairy cell leukemia, melanoma, non-small-cell lung cancer, pancreatic cancer, papillary thyroid cancer, and prostate cancer.

According to some of any of embodiments of the invention relating to a proliferative disease or disorder, the proliferative disease or disorder is associated with a mutation of a protein selected from the group consisting of NF1, Ras, Raf, MEK1/2 and ERK1/2.

According to some of any of embodiments of the invention relating to treating a disease or disorder, the treating comprises administration of at least one additional agent selected from the group consisting of a Raf inhibitor and a MEK inhibitor.

According to some of any of embodiments of the invention relating to a method of inhibiting nuclear translocation of ERK1/2 in a cell, the method is effected ex vivo.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
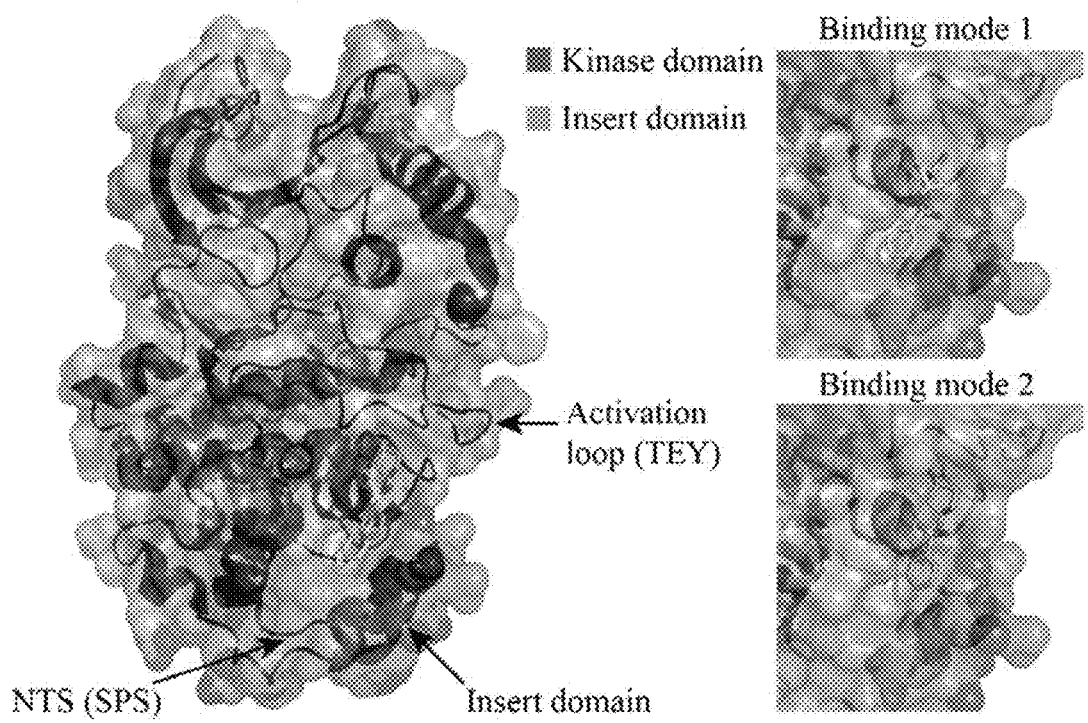
Figure 1B:
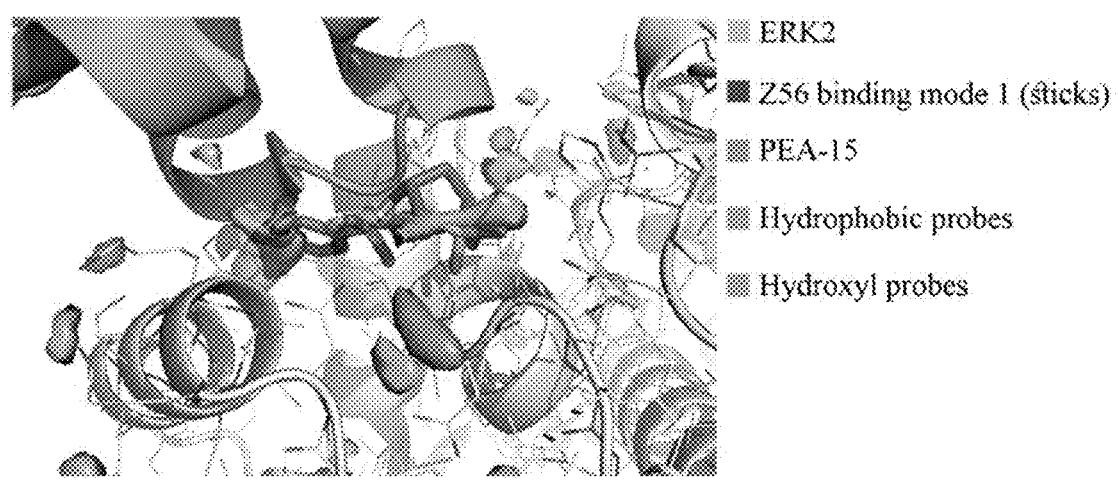

FIGS. 1A and 1B present in silico data showing Compound Z56 as a potential inhibitor of ERK1/2 nuclear translocation. FIG. 1A shows that Compound Z56 presents two binding modes. The Advanced Search tool of the PDB Database (www(dot)rcsb(dot)org) was used to perform a sequence search (BLAST), using the sequence of a reference structure (3W55) as query and an E-Value cutoff of 1E-100. The query returned 53 structures, corresponding to 32 Human ERK2 structures (Uniprot code P28482), 20 Rat ERK2 structures (Uniprot code P63086) and 1 Human ERK1 structure (Uniprot code P27361). All structures were loaded and structurally aligned using PyMOL. Structures were individually visualized looking for presence of organic molecules. Compound Z56 (ligand PDB code Q23) presents two different binding modes in PDB structure 3QYI (left). FIG. 1B presents simulations confirming binding of Compound Z56 to ERK2. MDmix simulation was carried out in order to assess the druggability and key interaction points of the site. High binding affinity areas for the hydrophobic (green) and hydroxyl (orange) probes are shown. Only the ERK2 protein (gray) was considered in the simulation. Binding mode 1 of Compound Z56 (molecule in sticks) and the part of PEA-15 that interacts with ERK2 (cyan) are overlaid for visualization purposes only.

Figure 2A:
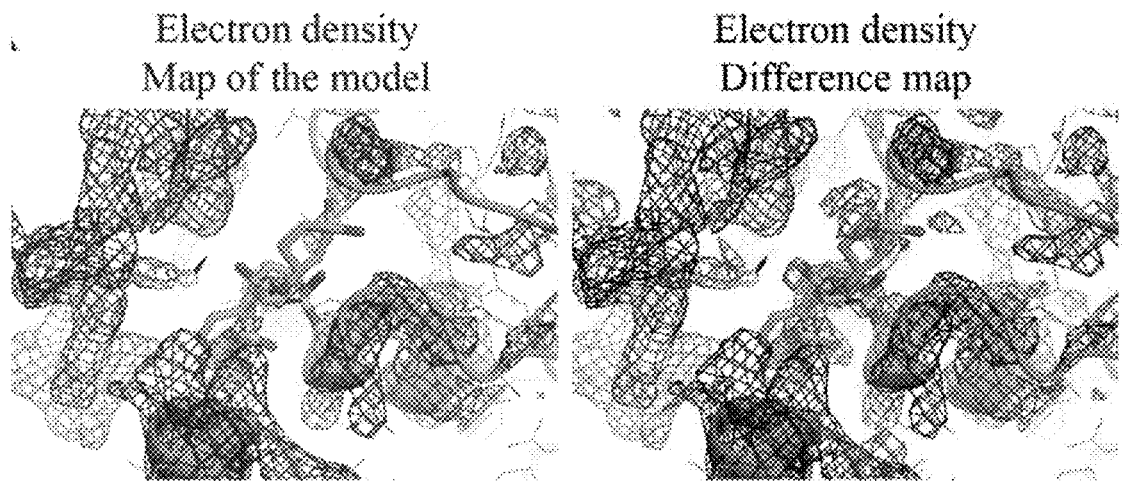
Figure 2B:
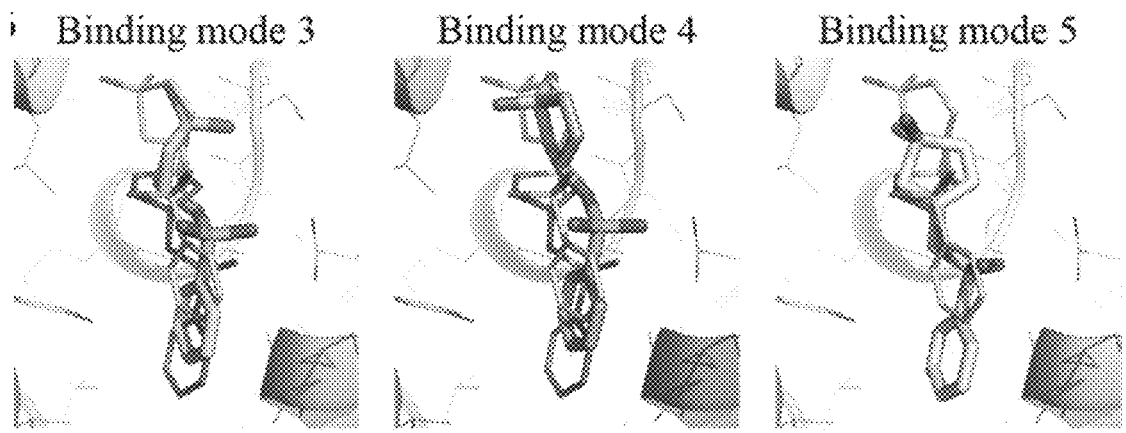
Figure 2C:
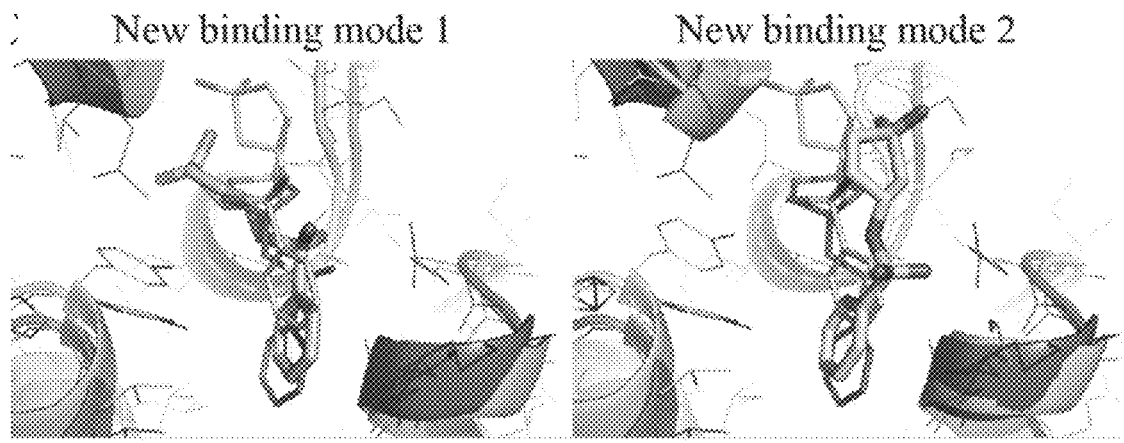

FIGS. 2A, 2B and 2C present data showing additional possible binding modes of Compound Z56 to ERK2. FIG. 2A shows that bindings modes in the PDB structure might not be accurate—(Left panel) Observed electron density (black mesh); (Right panel) Electron difference map showing areas with more (blue mesh) and less (red mesh) electron density. FIG. 2B presents additional binding modes considered for simulations. Three new proposed initial binding modes, binding mode 3 and 4 corresponding to the R and S enantiomer for a new position, and binding mode 5 which corresponds to the S enantiomer of binding mode 1. FIG. 2C presents molecular dynamics simulations and stable binding modes. Molecular dynamics simulations were carried out using the five initial binding modes. The aggregated simulations time reached was approximately 1 μsec (>60 GPU days). Two stable new binding modes (after 100 ns) are shown (crystallographic reported binding modes 1 and 2 displayed for reference in thin sticks).

Figure 3:
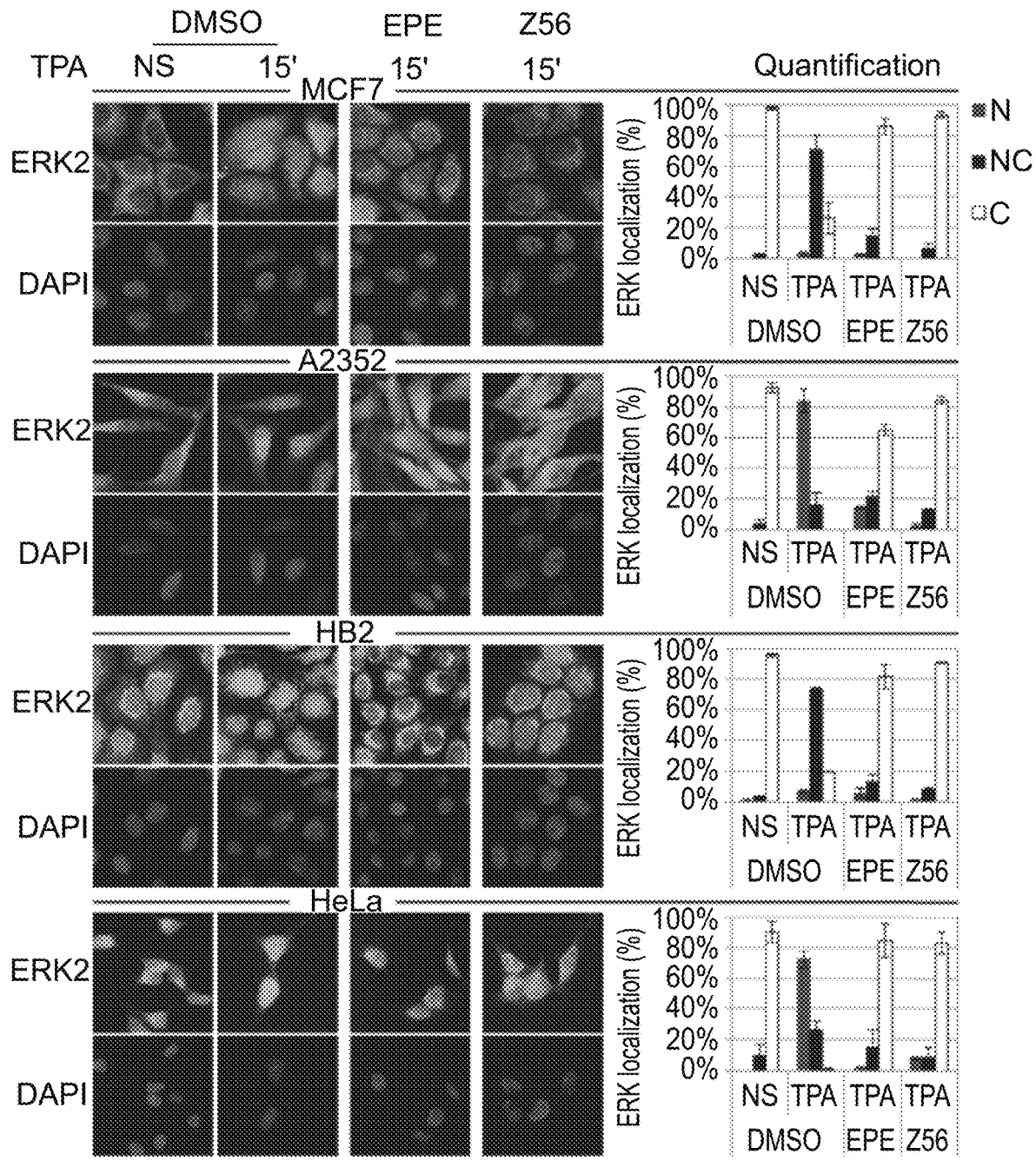

FIG. 3 presents data showing that Compound Z56 prevents the nuclear translocation of ERK1/2. The Compound Z56 has a similar effect on blocking the nuclear translocation of ERK1/2 compared to EPE peptide. (Left) MCF7, A2352, HB2 and HeLa cells were serum starved (0.1%, 16 hours), pretreated with Compound Z56 or EPE peptide (10 μM, 2 hours) or DMSO control (0.1%, 2 hours), and then stimulated with tetradecanoyl phorbol acetate (TPA; 100 nM, 15 minutes), or left non-stimulated. Cells were fixed and stained with αERK2 antibodies and DAPI. (Right) Bar graphs showing average ±SE of percentage of cells with nuclear ERK1/2 (N), nuclear and cytosolic (NC) or mostly cytosolic (C). Quantification was done by counting 6 fields per experiment each containing >50 cells. The experiments were produced in duplicates.

Figure 4A:
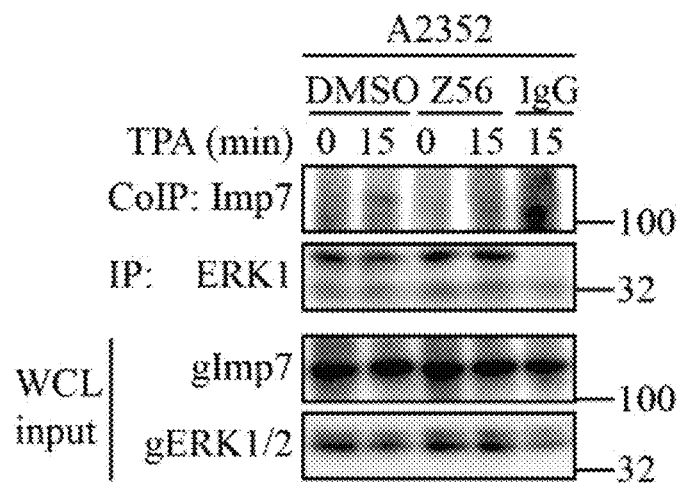
Figure 4B:
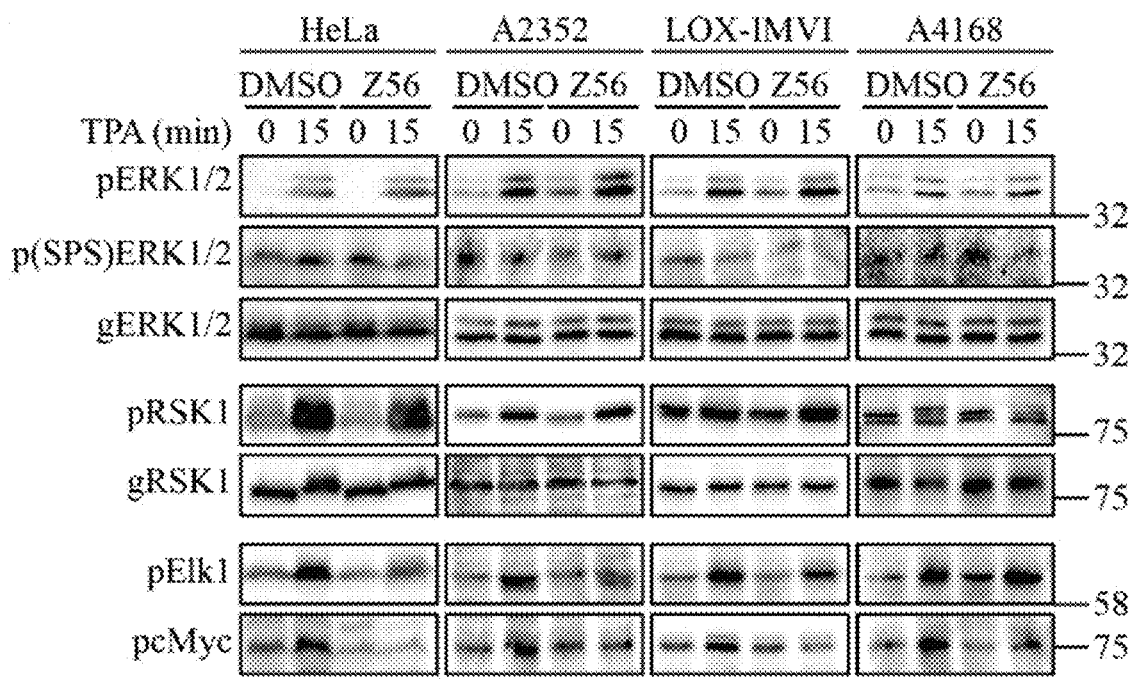
Figure 4C:
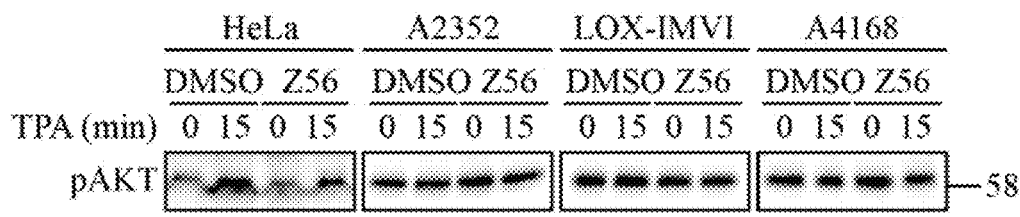

FIGS. 4A, 4B and 4C present data showing that Compound Z56 prevents ERK1/2-Importin7 interaction and activation of nuclear ERK1/2 targets. FIG. 4A shows that Compound Z56 prevents the interaction of ERK1 with Importin7. A2132 cells were serum starved (0.1%, 16 hours), pretreated with either DMSO (0.1%, 2 hours), or Compound Z56 (10 μM, 2 hours), and then stimulated with TPA (100 nM, 15 minutes) or left untreated. CoIP assay was conducted using αERK1 (C-terminus) antibodies conjugated to protein A/G agarose beads. The precipitates were analyzed by Western blot using the indicated antibodies. Whole cell lysates (WCL) and αIgG-mouse (IgG) are shown as controls. FIG. 4B shows that Compound Z56 prevents phosphorylation of Elk1, c-Myc and ERK1/2's NTS, but not RSK1 phosphorylation. HeLa, A2352, LOX-IMVI and A4168 cells were serum starved (0.1%, 16 hours), pretreated either with compound Z56 (10 μM, 2 hours) or DMSO control (0.1%), and then stimulated with TPA (100 nM, 15 minutes) or left untreated. Cell extracts were analyzed by Western blot with the indicated antibodies. FIG. 4C shows that Compound Z56 does not significantly affect short-term Akt phosphorylation in most cell lines. The same extracts described in (B) were subjected to Western blot analysis using αpAkt Abs. The closest molecular weight marker (kDa) is shown on the right of all relevant panels.

Figure 5A:
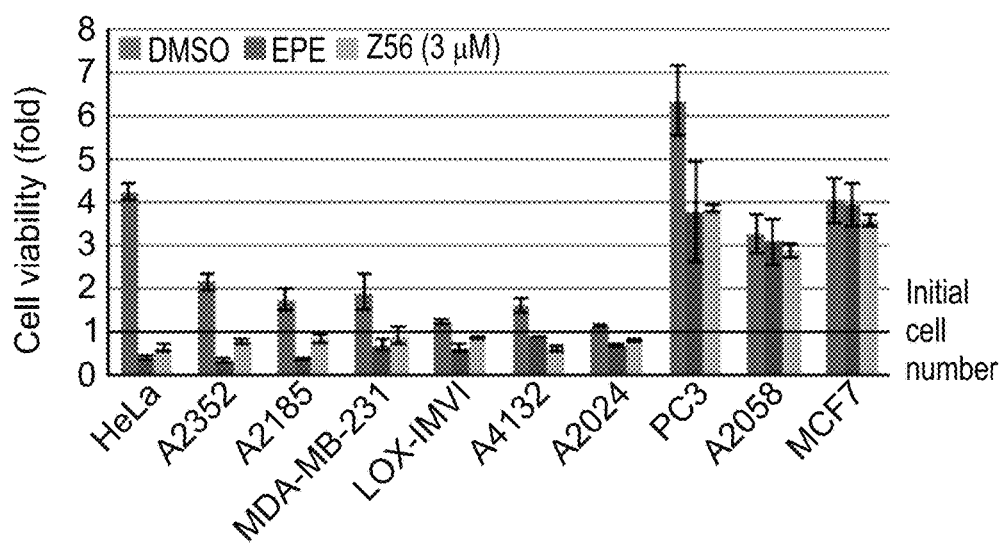
Figure 5B:
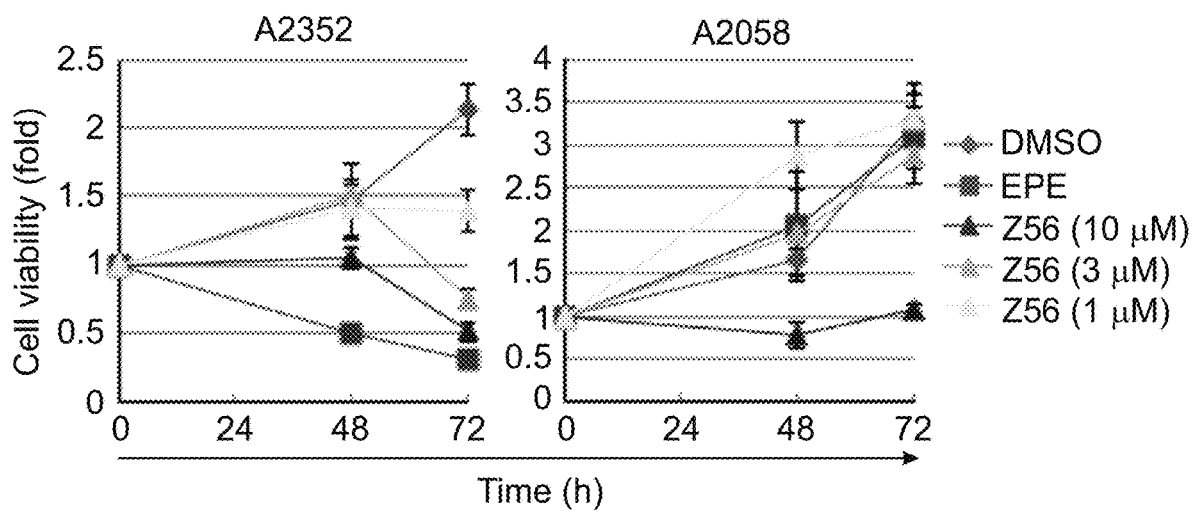

FIGS. 5A and 5B present data showing that Compound Z56 prevents proliferation of cancer cells.

FIG. 5A shows a comparison between the effects of the EPE peptide and Z56 on the proliferation of various cell lines. Ten cancer cell lines were treated with either EPE peptide (10 μM; middle bars) or Compound Z56 (3 μM; right bars) or DMSO control (0.1%; left bars) in 1% FCS (fetal calf serum) for 72 hours.

FIG. 5B shows the effect of Compound Z56 concentration on cell viability. A3252 and A2058 cells were treated either with EPE peptide (10 μM), Z56 (1, 3 or 10 μM) or DMSO control (0.1%). The graphs present the kinetics of cell proliferation at the indicated times. Viable cells were quantified by staining with methylene blue. All results were presented as a fold change of the initial cell number and represent averages ±SE of 3 experiments in triplicate.

Figure 6A:
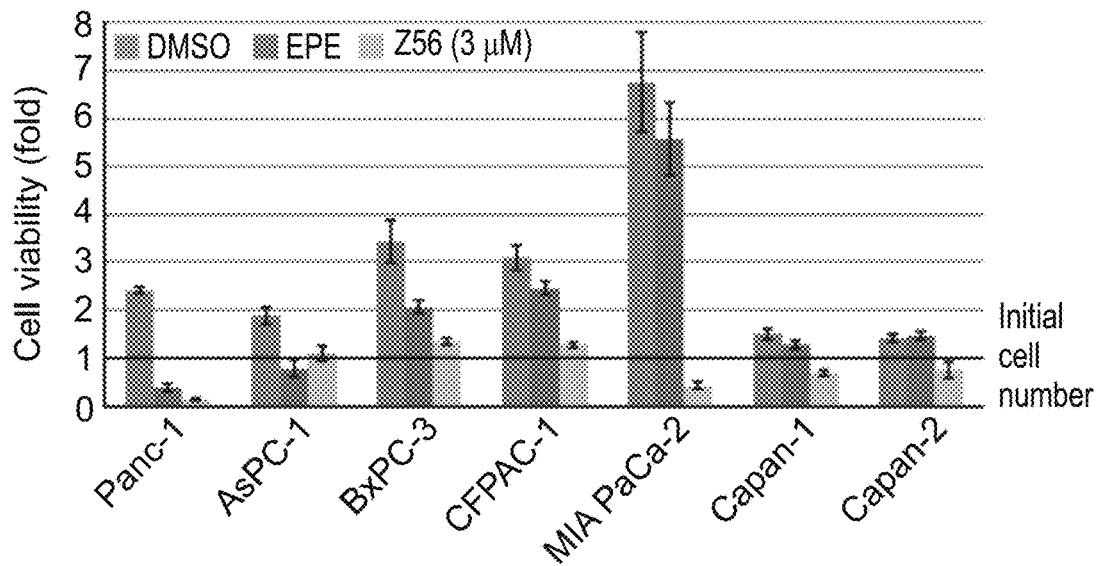
Figure 6B:
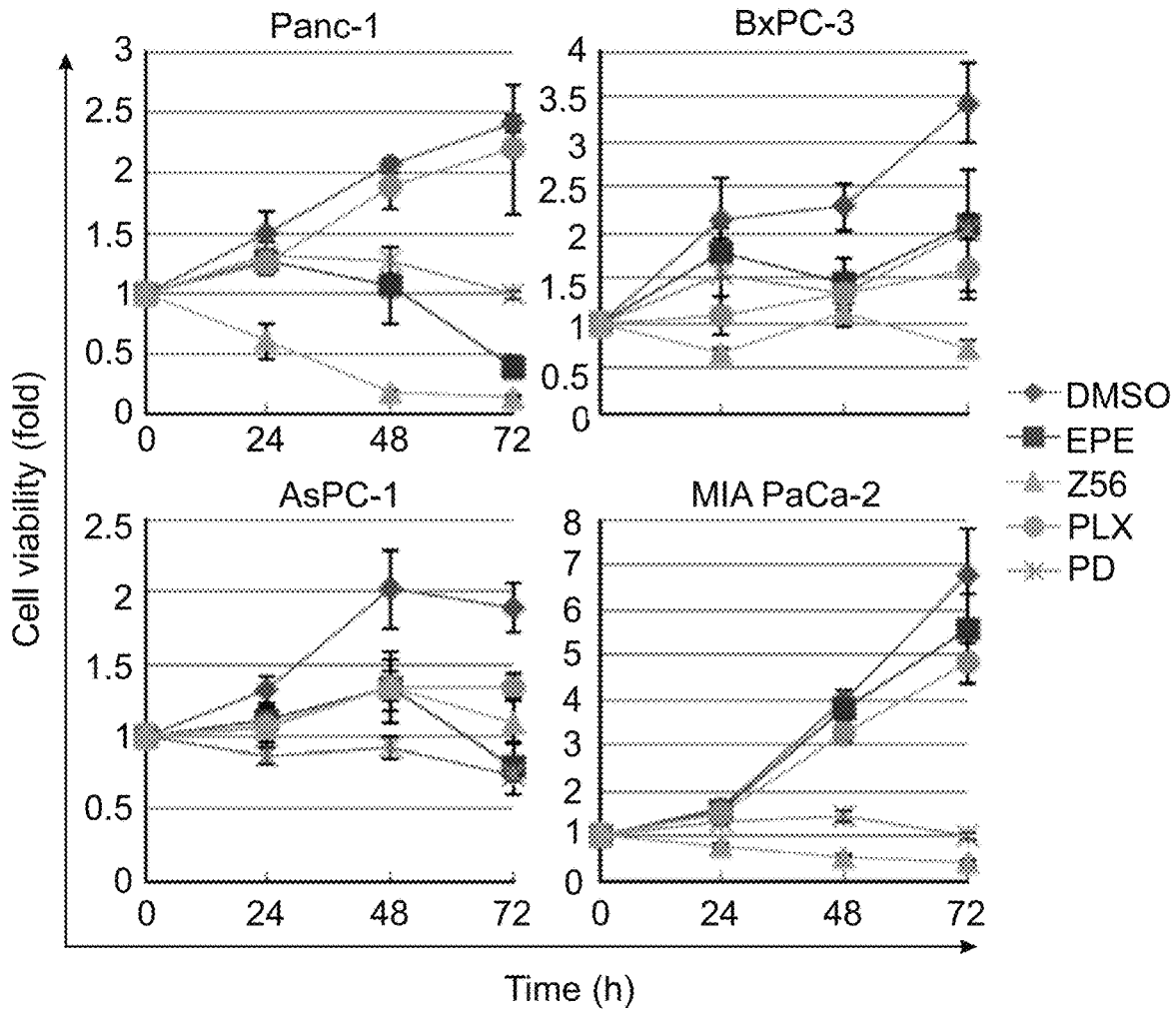

FIGS. 6A and 6B present data showing that Compound Z56 prevents proliferation of pancreatic cancer cells. FIG. 6A shows a comparison between the effects of the EPE peptide and Compound Z56 on the proliferation of seven pancreatic cell lines. Panc-1, AsPC-1, CFPAC-1, Mia PaCa-2, Capan-1, Capan-2 (Ras-transformed) and BxPC-3 (Ras-wild type) pancreatic cancer cells were treated with either EPE peptide (10 μM; middle bars) or Z56 (3 μM; right bars) or DMSO control (0.1%; left bars) in 1% FCS for 72 hours. FIG. 6B shows a comparison of the effects of Compound Z56 with Raf inhibitor PLX4032 and MEK1/2 inhibitor PD184352 on cell viability. Panc-1, AsPC-1, BxPC-3 and Mia PaCa-2 cells grown in 1% FCS medium containing either EPE peptide (10 μM), 56 (3 μM), PLX4032 (1 μM), PD184352 (5 μM) or DMSO control (0.1%). The graphs present the kinetics of cell proliferation at the indicated times after the treatment started. Quantification of all viable cells was done by methylene blue and repeated 3 times in triplicates. All results presented as a fold change of the initial cell number and represent averages ±SE.

Figure 7A:
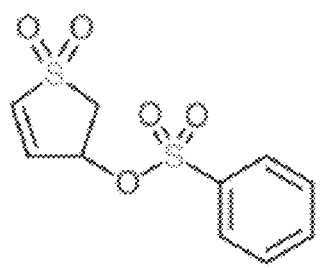
Figure 7A:
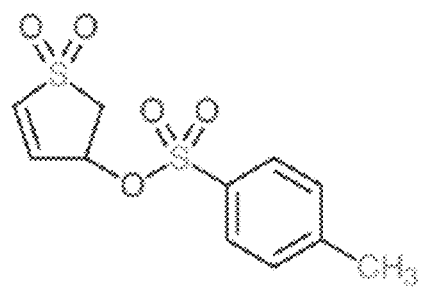
Figure 7A:
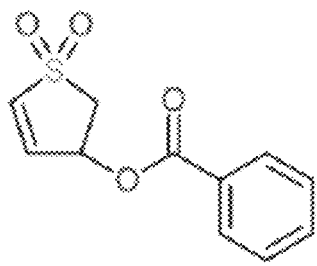
Figure 7A:
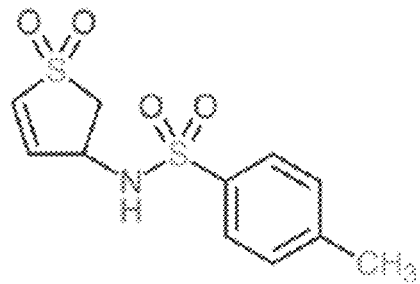
Figure 7B:
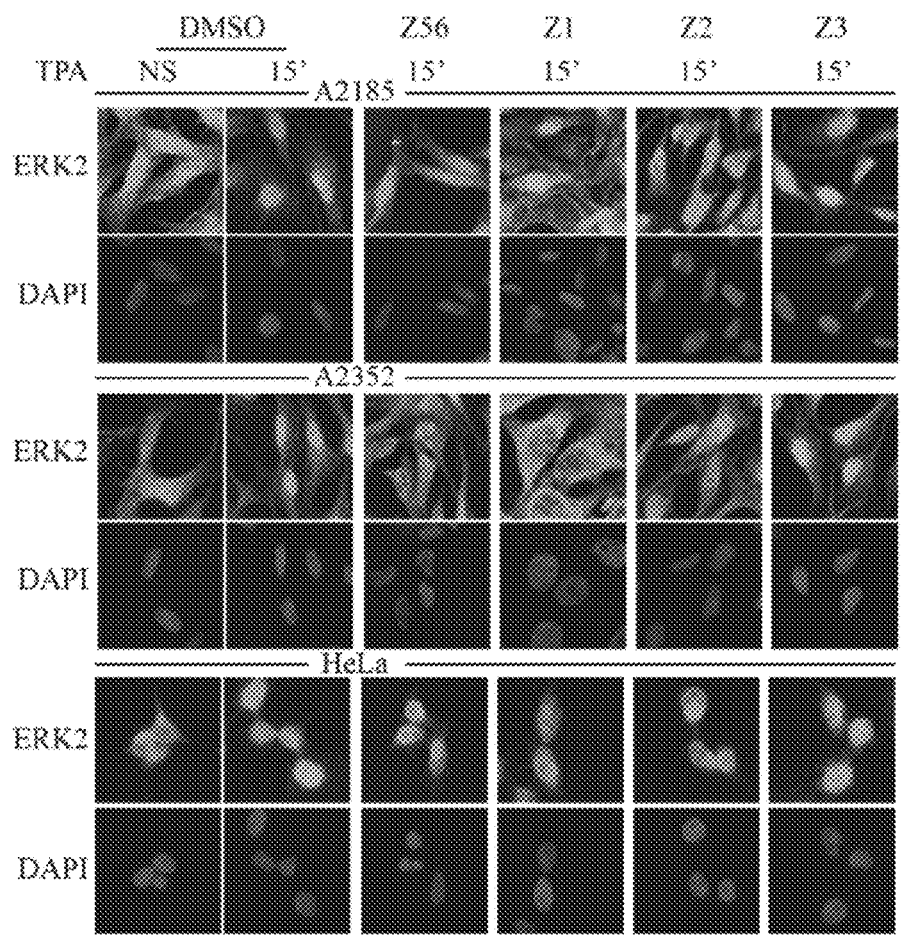
Figure 7C:
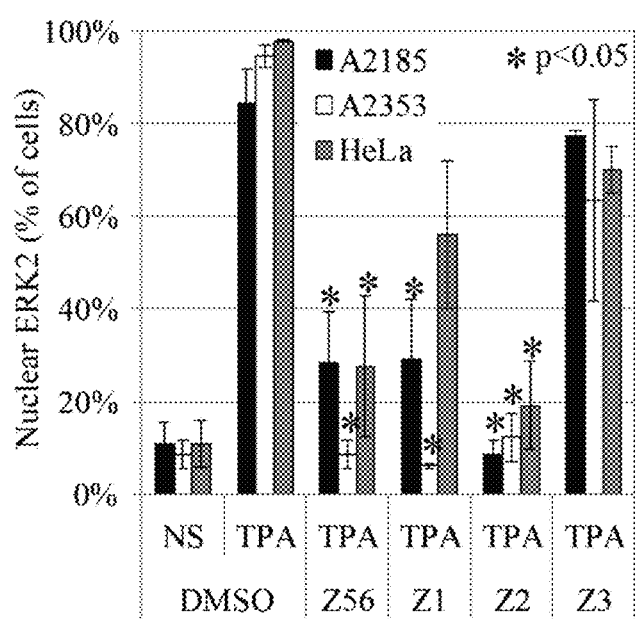

FIGS. 7A, 7B and 7C present data showing effects of chemical analogs of Compound Z56 on ERK1/2 nuclear translocation. FIG. 7A shows the structure of Z56 and three chemical modifications of Compound Z56 which were tested: Compound Z1 (p-toluene analog), Compound Z2 (ester analog) and Compound Z3 (sulfonamide plus p-toluene analog). FIG. 7B shows that Compounds Z1 and Z2 retain ERK1/2 nuclear translocation inhibitory activity. A2352, A2185 and HeLa cells were serum starved (0.1%, 16 hours), pretreated with either DMSO (0.1%) or compounds Z56, Z1, Z2 or Z3 (10 μM) for 2 hours, and stimulated with TPA (100 nM, 15 minutes) or left untreated. Nuclear translocation of ERK1/2 was followed using αERK2 antibodies and DAPI. FIG. 7C presents quantification done by counting 3-4 fields, each with >50 cells. Bar graphs represent average percentage of cells with mostly nuclear ERK1/2 localization ±SE. Experiments done in duplicates. (*) $p<0.05$ by Student's t-test two tails.

Figure 8A:
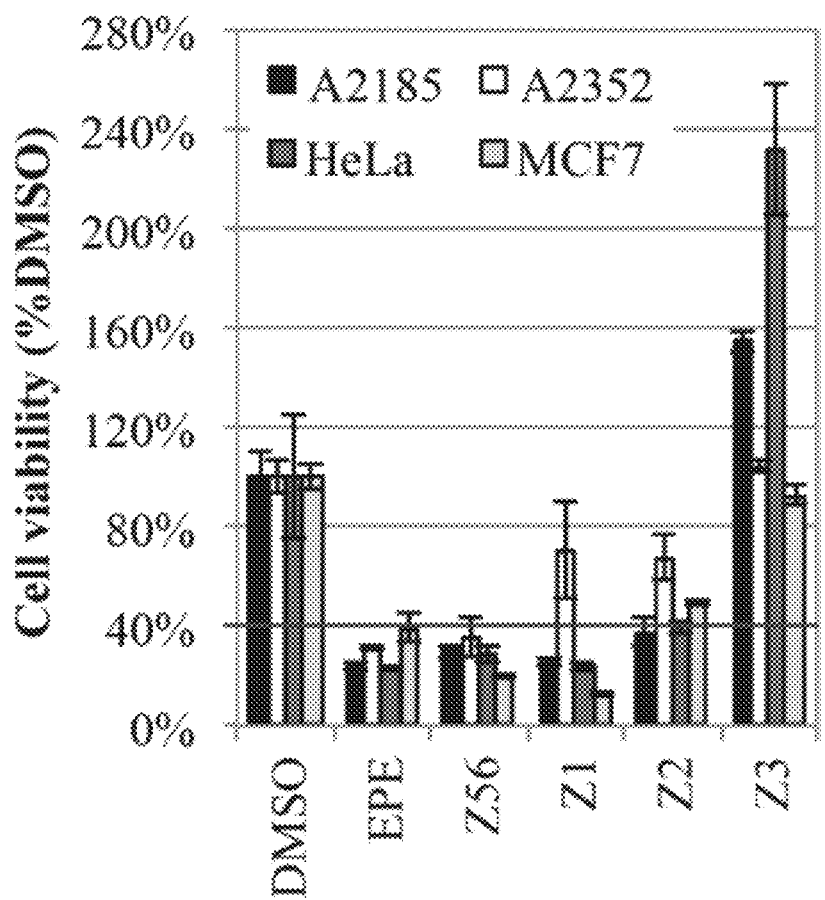
Figure 8B:
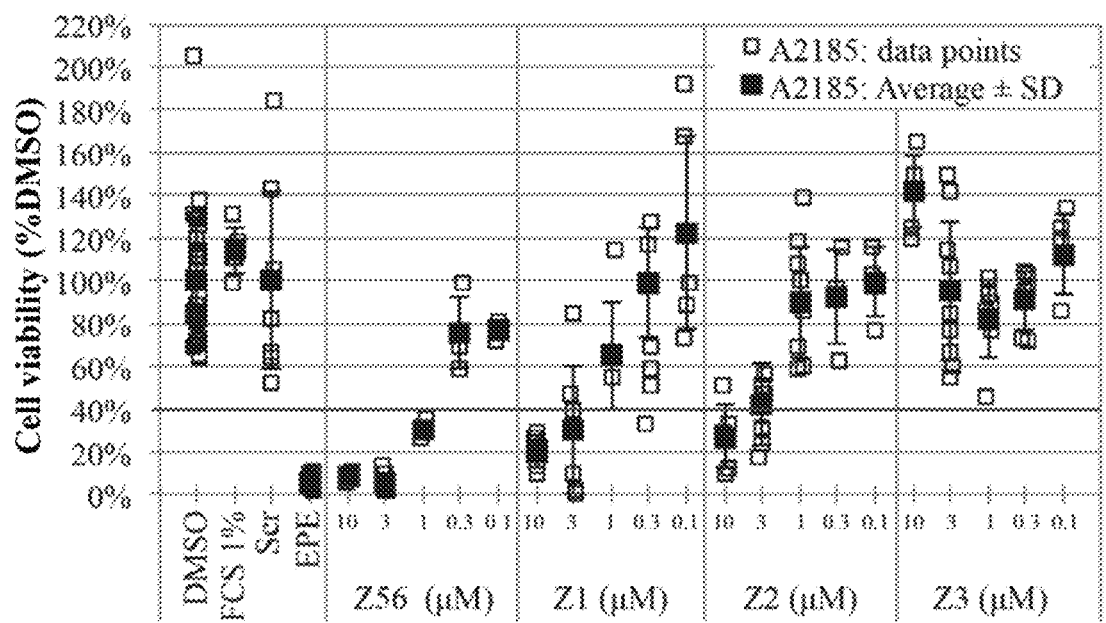
Figure 8C:
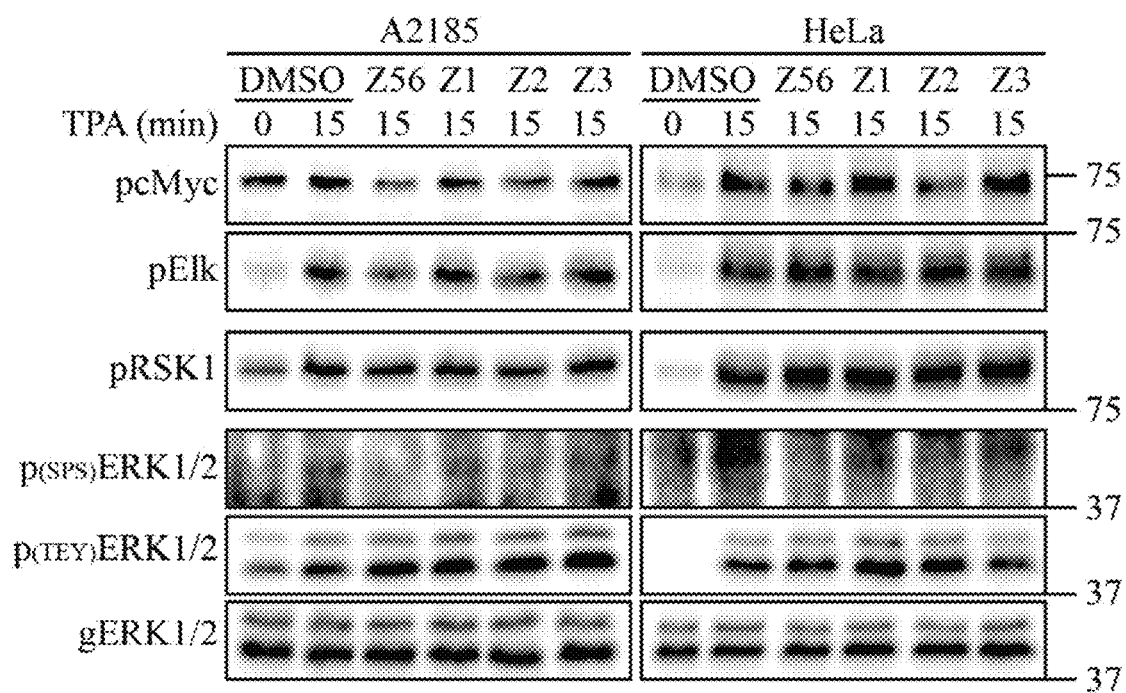

FIGS. 8A, 8B and 8C present data showing that Compound Z2, the ester analog of Z56, is superior as a lead molecule. FIG. 8A shows effects of analogs of Z56 on proliferation of cancer cells. Four cancer cells, A2185, A2352, HeLa and MCF7 were grown in 1% FCS containing 10 μM of either EPE peptide, or Compounds Z56, Z1, Z2 or Z3, for 72 hours. Bars indicate average of 2 independent experiments done in triplicate ±SE. FIG. 8B presents dose response curves for Compounds Z56, Z1 and Z2. A2185 cells were grown in 1% FCS containing DMSO (0.1%) EPE or Scramble (Scr) peptide (10 μM), Compounds Z56, Z1, Z2, Z3 (0.1-10 PM) or no treatment (FCS 1%) for 72 hours. Empty squares represent individual data points of proliferation. Full squares indicate average proliferation of 2 independent experiments done in triplicate ±SE. Bold horizontal line indicates arbitrary threshold (40%) for what is considered an active compound. Cell viability (as shown in FIGS. 8A and 8B) was measured by staining with methylene blue, and data presents proliferation normalized to DMSO control. FIG. 8C shows that Compounds Z56 and Z2 reduce phosphorylation of ERK1/2 nuclear targets. A2185 and HeLa cells were serum starved (0.1%, 16 hours), pretreated with DMSO (0.1%), or Compounds Z56, Z1, Z2 or Z3 (10 μM) for 2 hours, and stimulated with TPA (100 nM, 15 minutes). Cell lysates were analyzed by Western blot with the corresponding antibodies. Closest molecular marker is indicated at the right of each panel.

Figure 9:
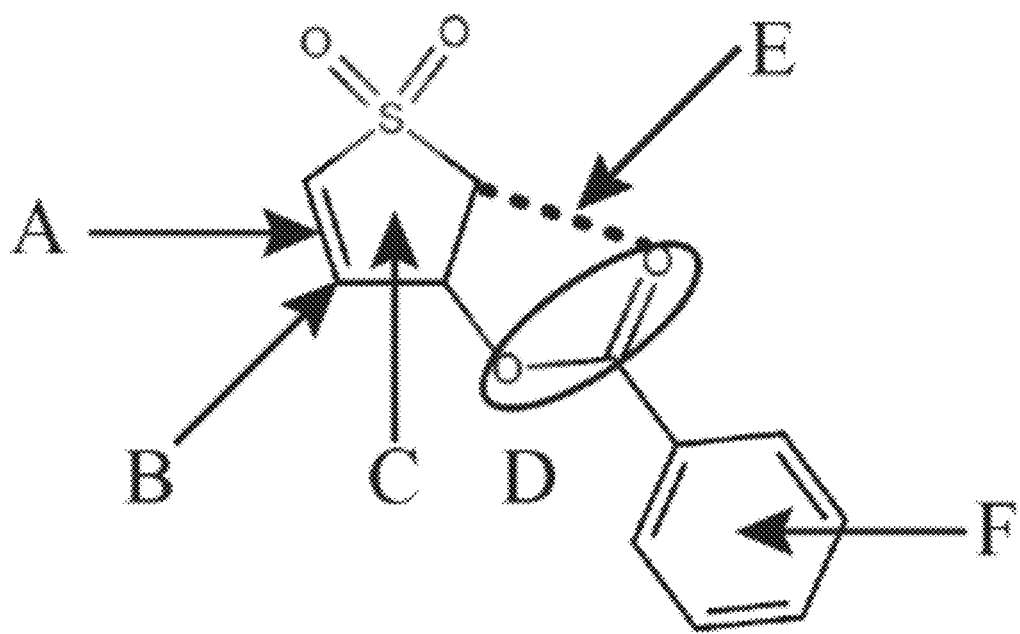

FIG. 9 presents the sites of modifications (A-F) in the structure of Compound Z2, represented by exemplary compounds ("C-compounds") used for structure activity relationship studies.

Figure 10A:
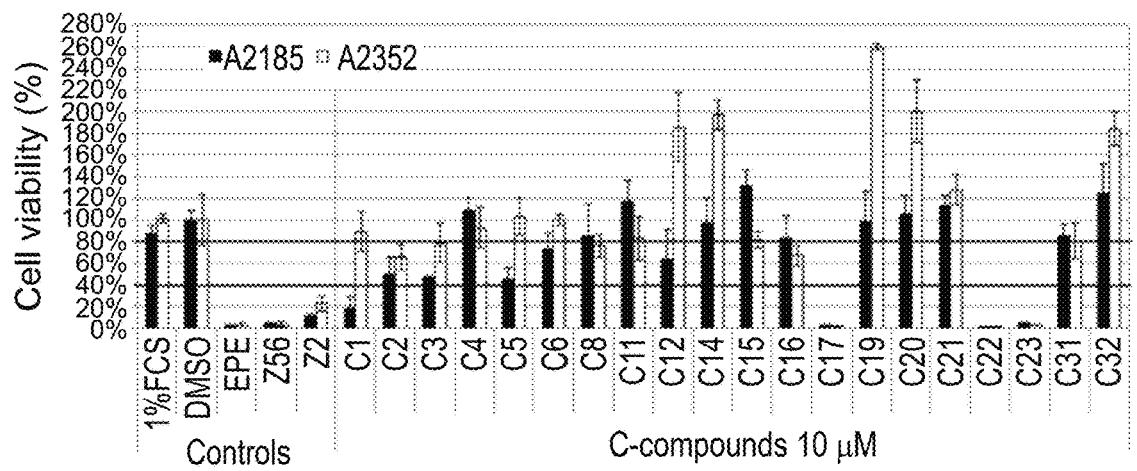
Figure 10B:
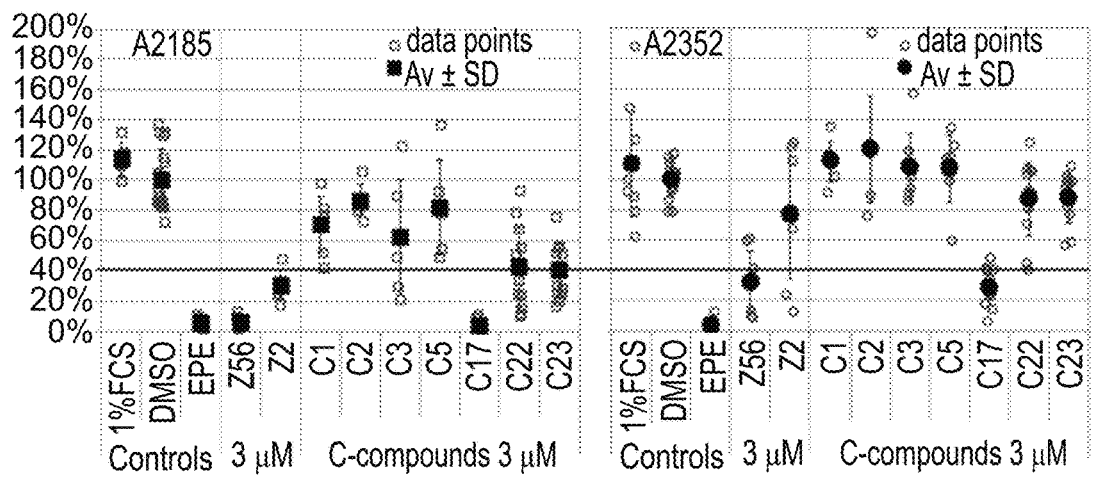
Figure 10C:
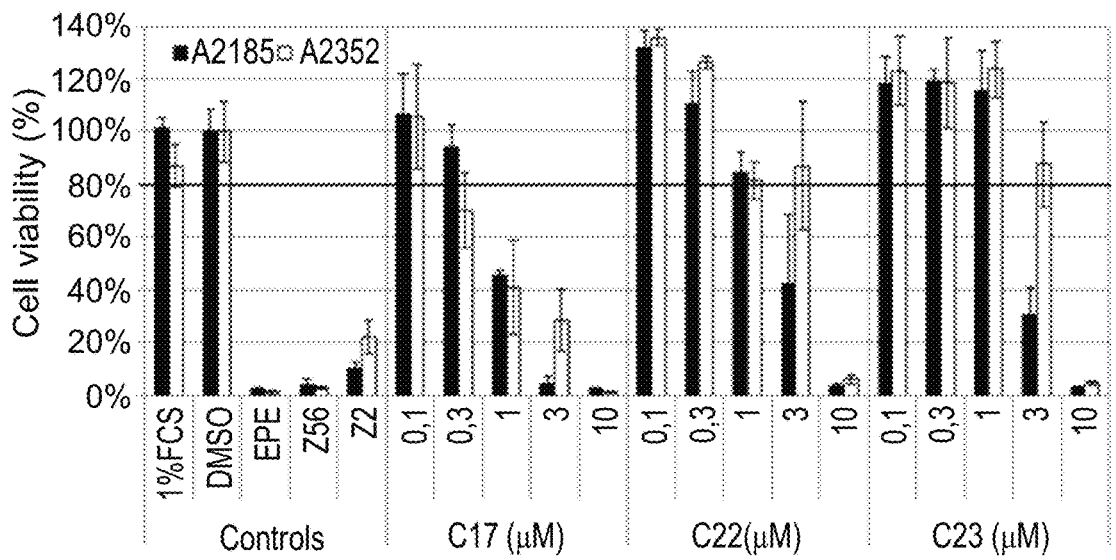

FIGS. 10A, 10B and 10C present data from screening the 20 analogs of Compound Z2 ("C-compounds") showing three particularly active anti-proliferative compounds. FIG. 10A shows proliferation screening of C-compounds at high concentration. A2185 and A2352 cells were grown in 1% FCS containing DMSO (0.1%), EPE peptide, Compound Z56, Compound Z2 or C-compounds (10 μM), for 72 hours. Compounds were categorized according to activity: (1) active, below 40%; (2) moderate activity, below 80%; (3) not active, above 80%. FIG. 10B shows activity of compounds at low concentration. A2185 and A2352 cells were grown in 1% FCS containing DMSO (0.1%), EPE peptide (10 μM), compounds Z56, Z2 or selected C-compounds (3 μM), for 72 hours. Empty squares/circles represent individual data points of proliferation. Full squares/circles indicate average proliferation of 2 independent experiments in triplicate±SE. Bold horizontal line defines arbitrary activity threshold of activity below 40%. FIG. 10C presents dose response curves of active C-compounds compounds. A2185 and A2352 were grown in 1% FCS media containing DMSO (0.1%), EPE peptide, Z56, Z2 (10 μM) or compounds C17, C22 and C23 (0.1-10 μM), for 72 hours. Bold horizontal line shows arbitrary threshold at 80%. Cell viability was measured by staining with methylene blue. Data presented as percentage of DMSO control. Bar graphs represent average of 2 independent experiments done in triplicates ±SE.

Figure 11A:
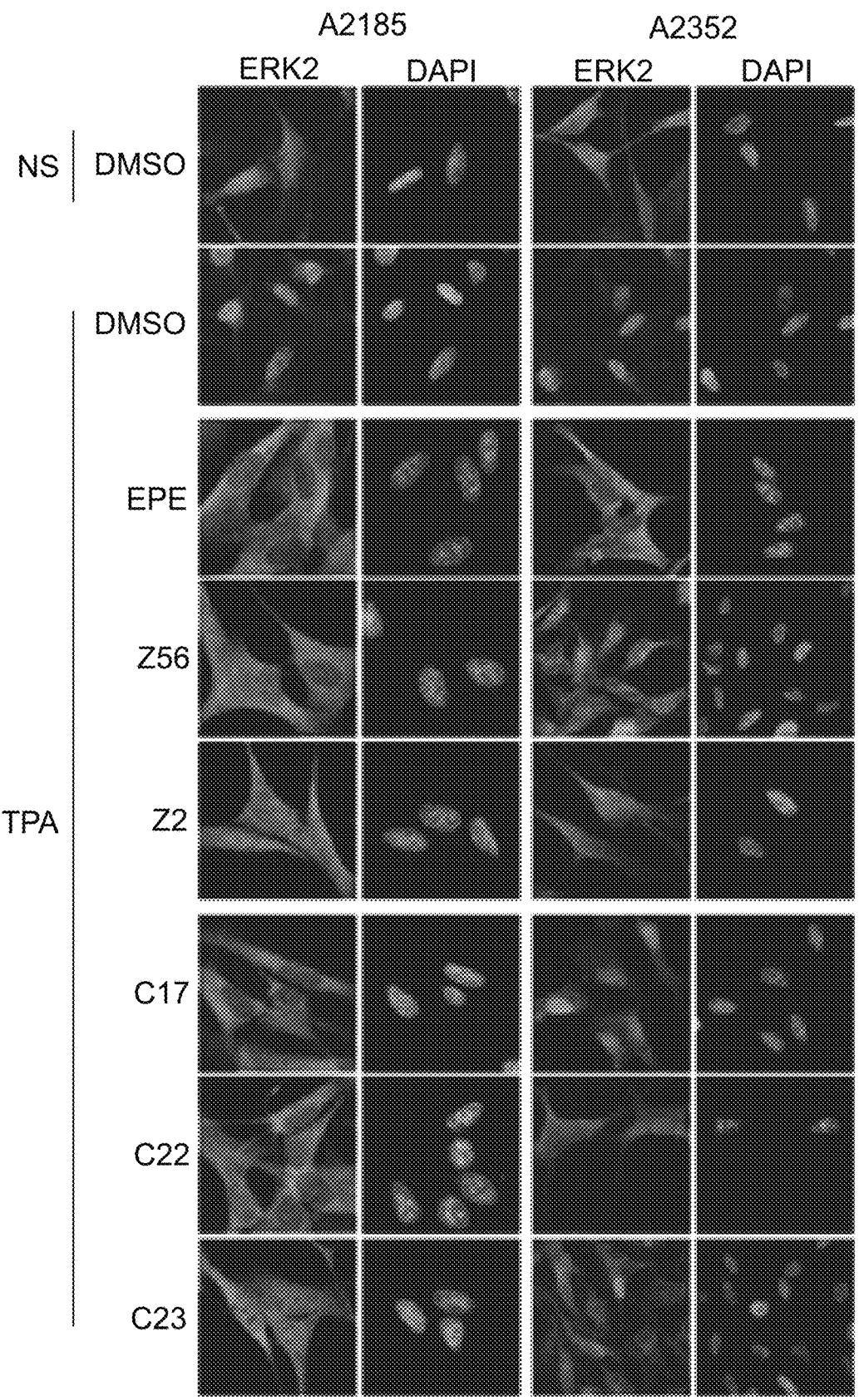
Figure 11B:
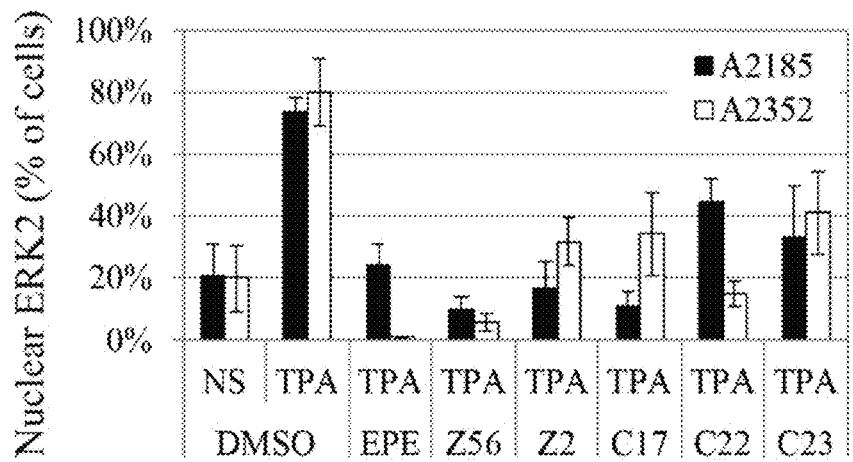
Figure 11C:
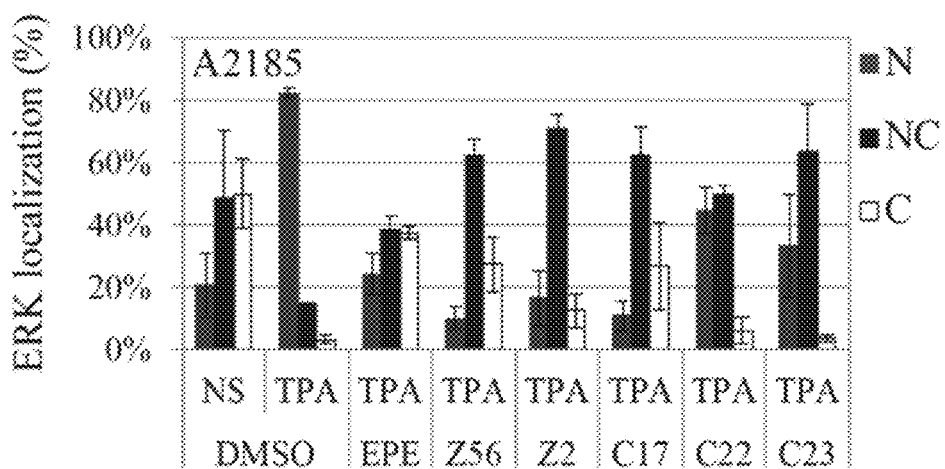

FIGS. 11A, 11B and 11C present data showing that Compounds C17, C22 and C23 block the nuclear accumulation of ERK1/2. FIG. 11A shows that Compounds C17, C22 and C23 inhibit the stimulated nuclear accumulation of ERK1/2. A2185 and A2352 cells where serum-starved (0.1%, 16 hours), pretreated with DMSO (0.1%), EPE peptide or Compounds Z56, Z2, C17, C22 or C23 (10 μM, 2 hours), and stimulated with TPA (100 nM, 15 minutes) or left untreated. Nuclear translocation of ERK1/2 was detected by immunostaining with αERK2 (C-14) antibodies and DAPI. FIG. 11B presents quantification of A2185 and A2352 cell staining, done by counting of 3 or 4 fields (total >150 cells). Data presented as percentage of cells with mostly nuclear ERK1/2 localization. FIG. 11C presents quantification of A2185 cells showing percentage of cells with mostly nuclear localization (N; left bars), nuclear and cytosolic (NC; middle bars) and mostly cytosolic localization (C; right bars). Bar graphs represent average of two independent experiments done in duplicates ±SE.

Figure 12:
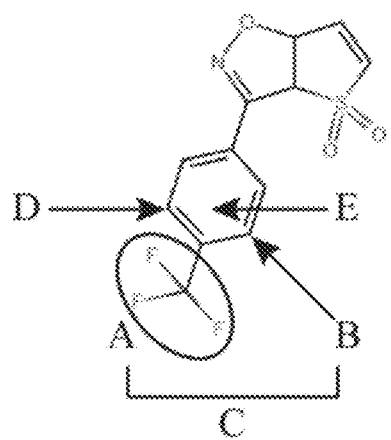

FIG. 12 presents the sites of modifications (A-E) in the structure of C17, represented by exemplary compounds ("D-compounds") used for structure activity relationship studies.

Figure 13:
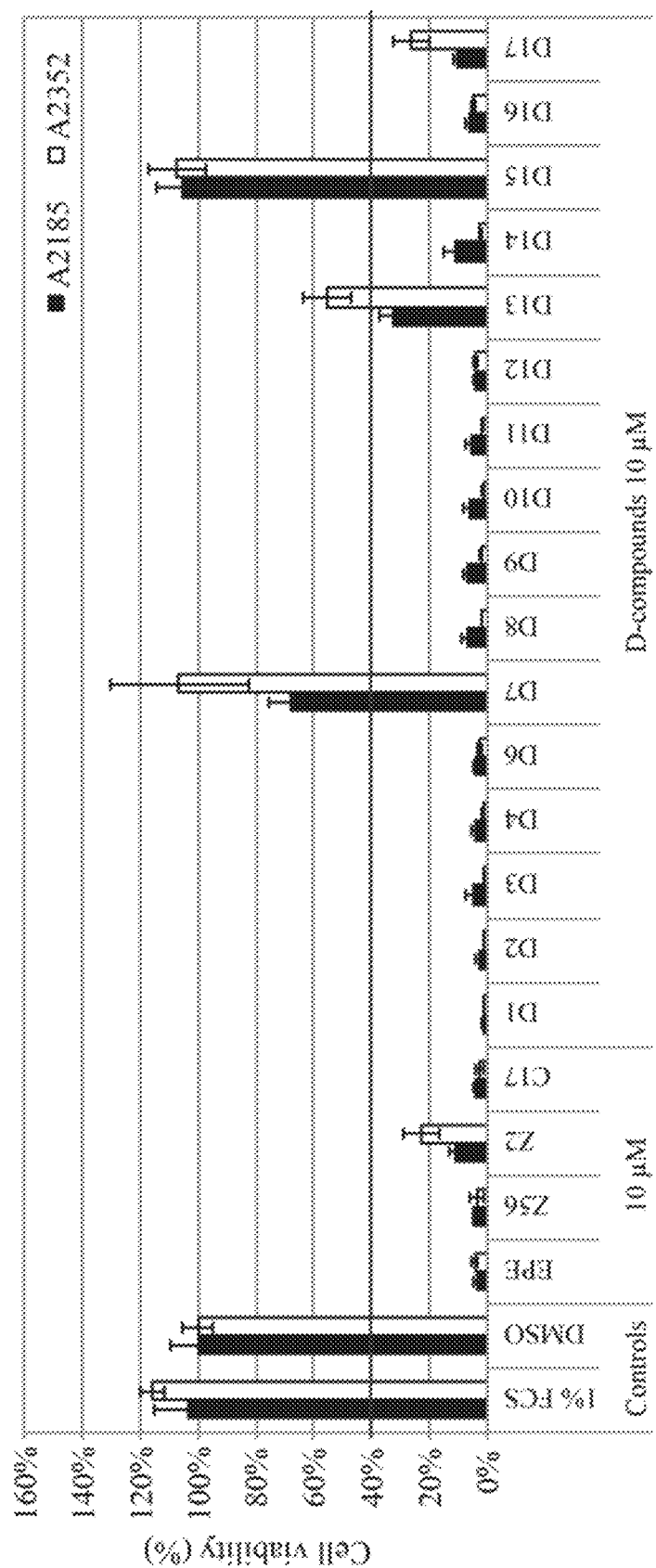

FIG. 13 presents a graph showing the effect of analogs of Compound C17 ("D-compounds") on cell viability at a concentration of 10 μM. A2185 and A2352 cells were grown in 1% FCS media containing DMSO (0.1%) EPE peptide (10 μM), Compounds Z56, Z2, C17 (10 μM) as controls, and D-Compounds (10 μM), for 72 hours. Viable cells were measured by staining with methylene blue. Bar graphs represent average of 2 independent experiments done in triplicates. Data presented as percentage of DMSO proliferation ±standard error.

Figure 14:
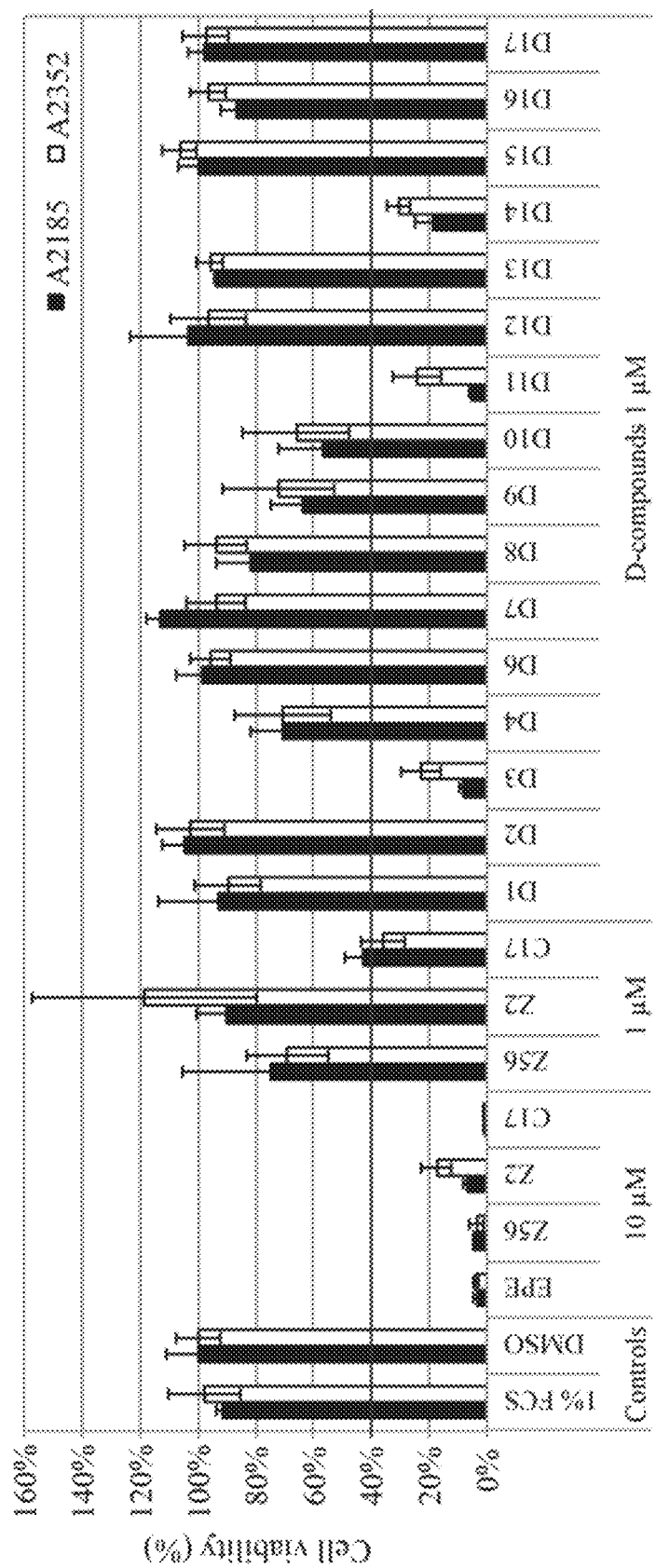

FIG. 14 presents a graph showing the effect of analogs of Compound C17 ("D-compounds") on cell viability at a concentration of 1 μM. A2185 and A2352 cells were grown in 1% FCS media containing DMSO (0.1%), EPE peptide (10 μM), Compounds Z56, Z2 and C17 (1 and 10 μM) as controls, and D-compounds (1 μM), for 72 hours. Viable cells were measured by staining with methylene blue. Bar graphs represent average of 2 independent experiments done in triplicates. Data presented as percentage of DMSO proliferation ±standard error.

Figure 15A:
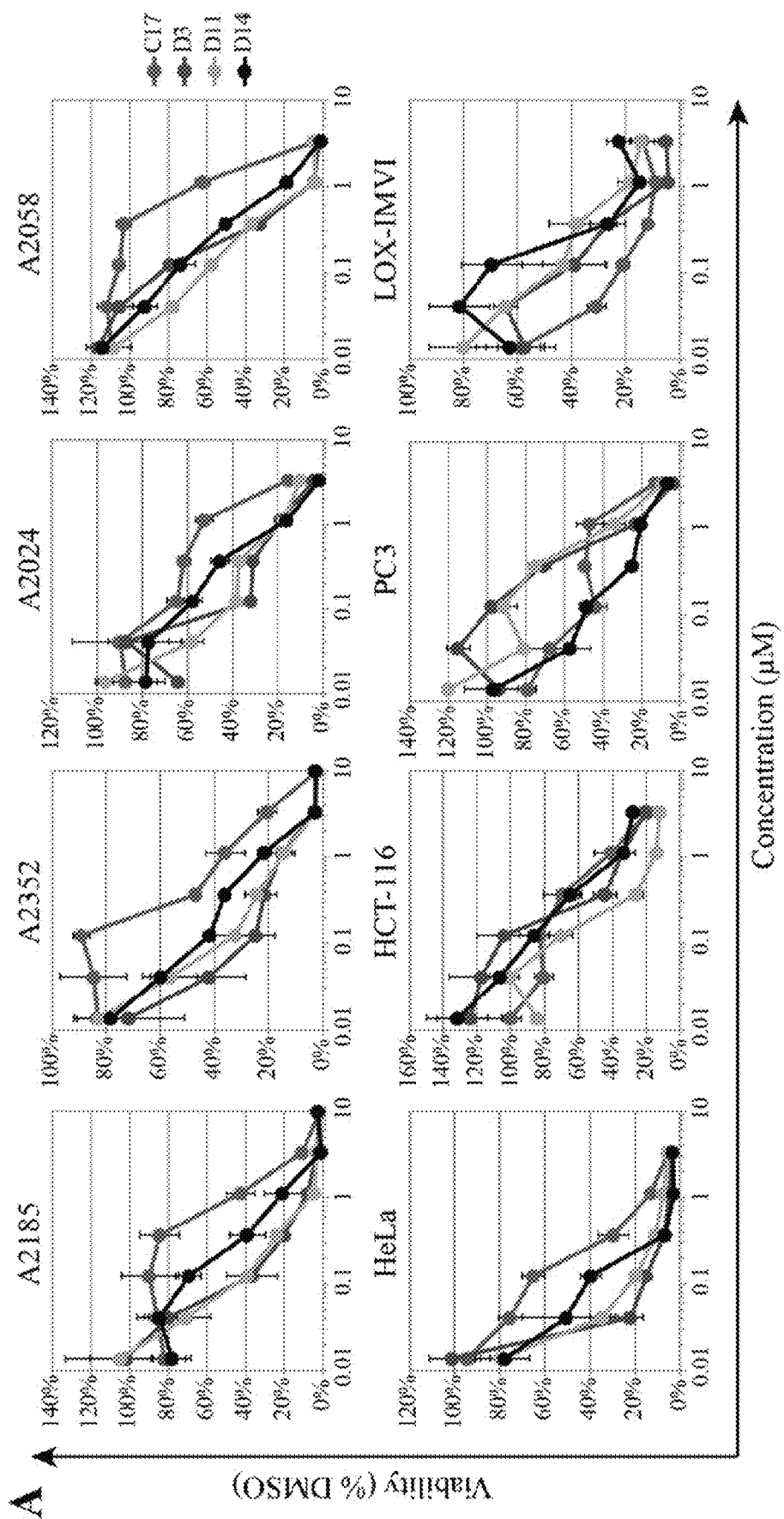
Figure 15B:
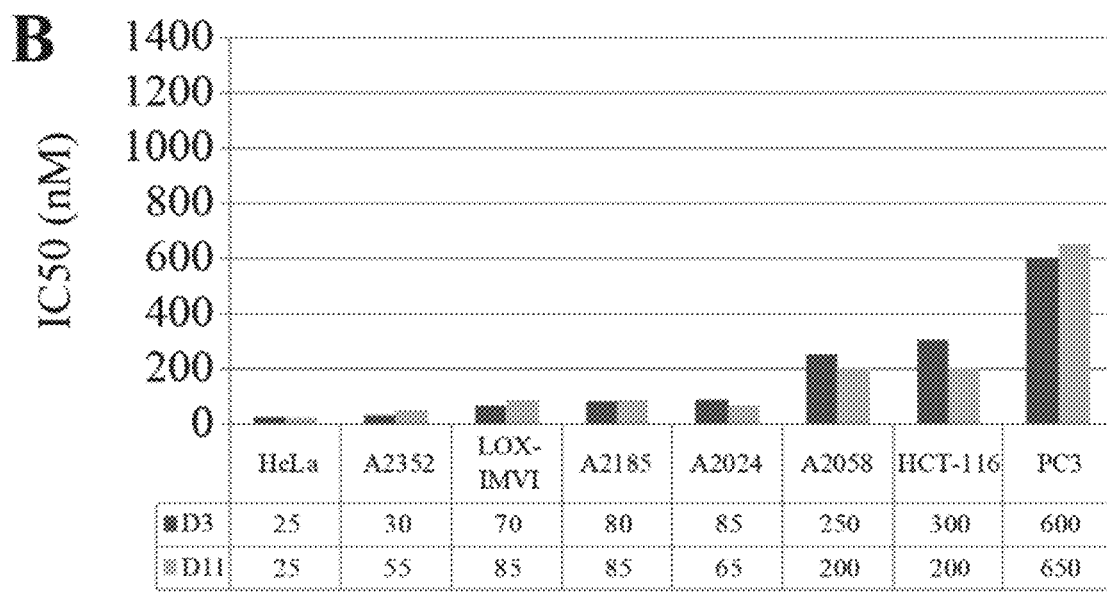
Figure 15B:
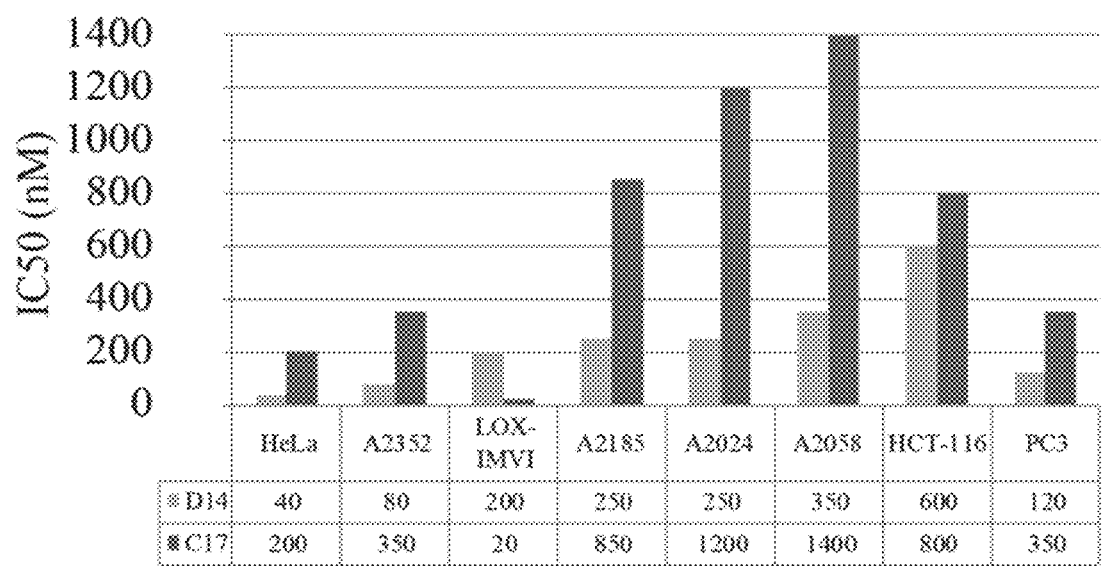
Figure 15C:
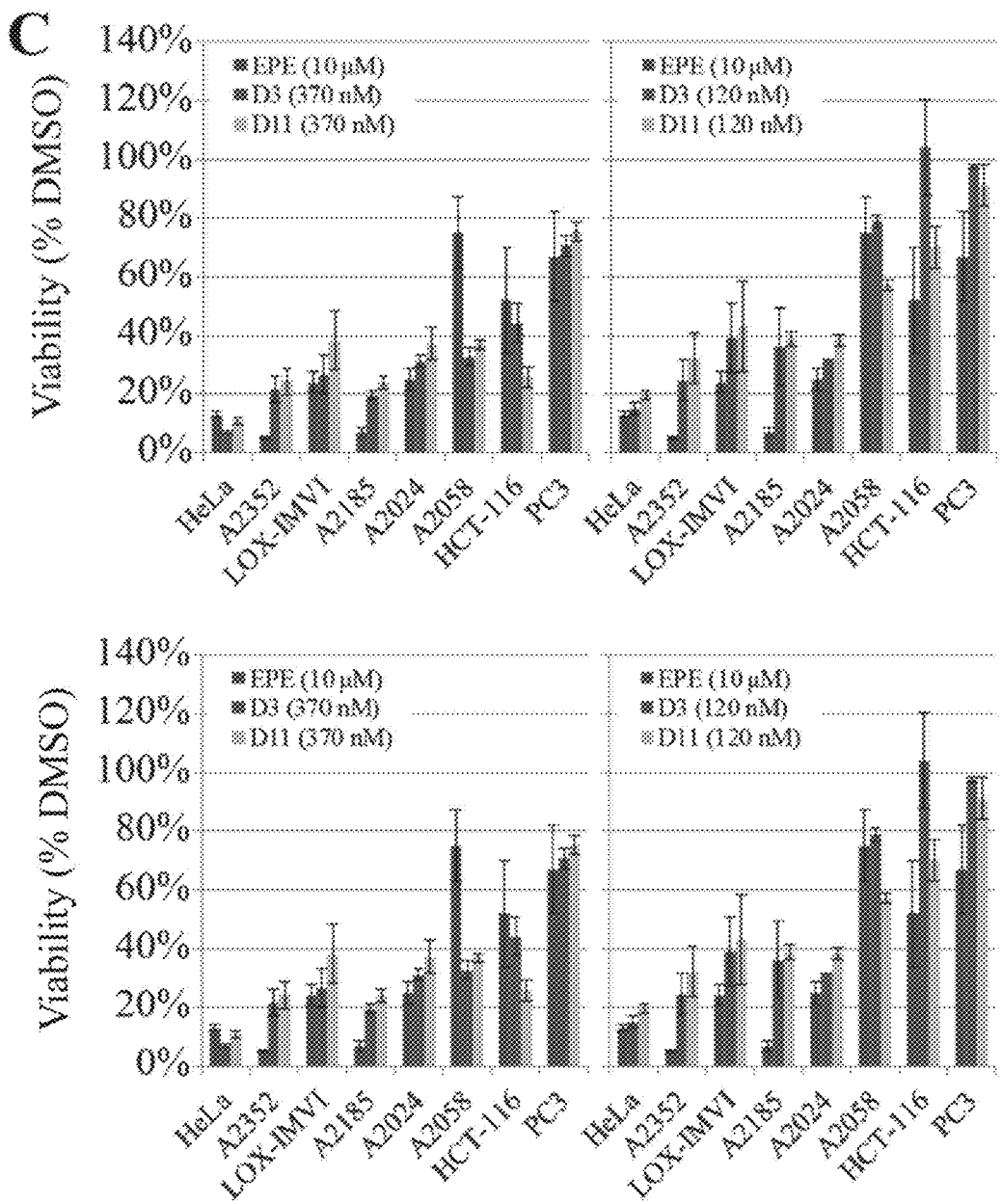

FIGS. 15A, 15B and 15C presents data showing that Compounds D3, D11 and D14 exhibit enhanced activity. FIG. 15A presents dose response curves of compounds C17, D3, D11 and D14 on 8 cancer cells. Five melanoma cell lines (A2185, A2352, A2024, A2058 and LOX-IMVI), HeLa, HCT-116 and PC3 cells were grown in 1% FCS media containing either DMSO (0.1%), EPE peptide (10 μM), or Compounds C17, D3, D11, D14 at the indicated concentrations, for 72 hours. Viable cells were quantified by staining with methylene blue. Data presented as percentage of DMSO control ±SE of triplicates. FIG. 15B shows that Compounds D3 and D11 are more potent than C17 and D14. $IC_{50}$ values were calculated by interpolation in the curves in FIG. 15A. FIG. 15C shows that Compounds D3 (middle bars) and D11 (right bars) have similar selectivity compared to EPE peptide (left bars) at low concentration. Bar graphs represent average viability respect to DMSO control ±SE of triplicates.

Figure 16:
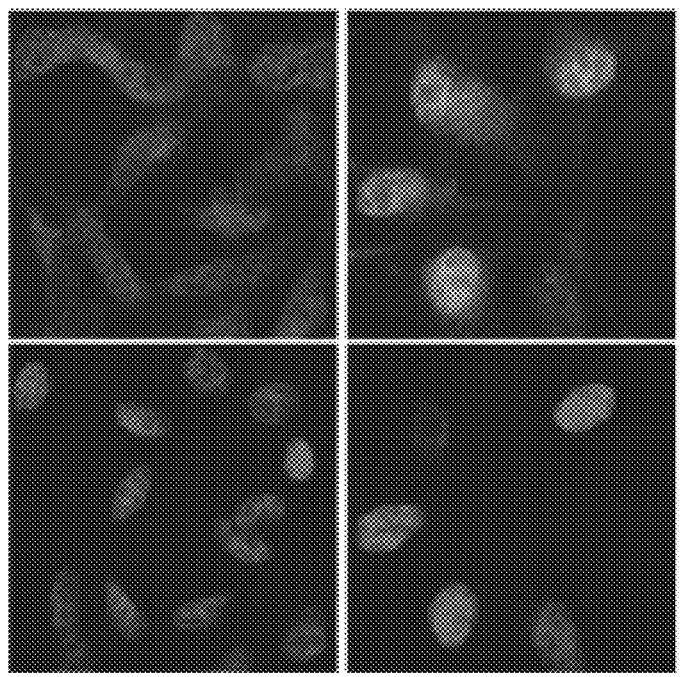
Figure 16:
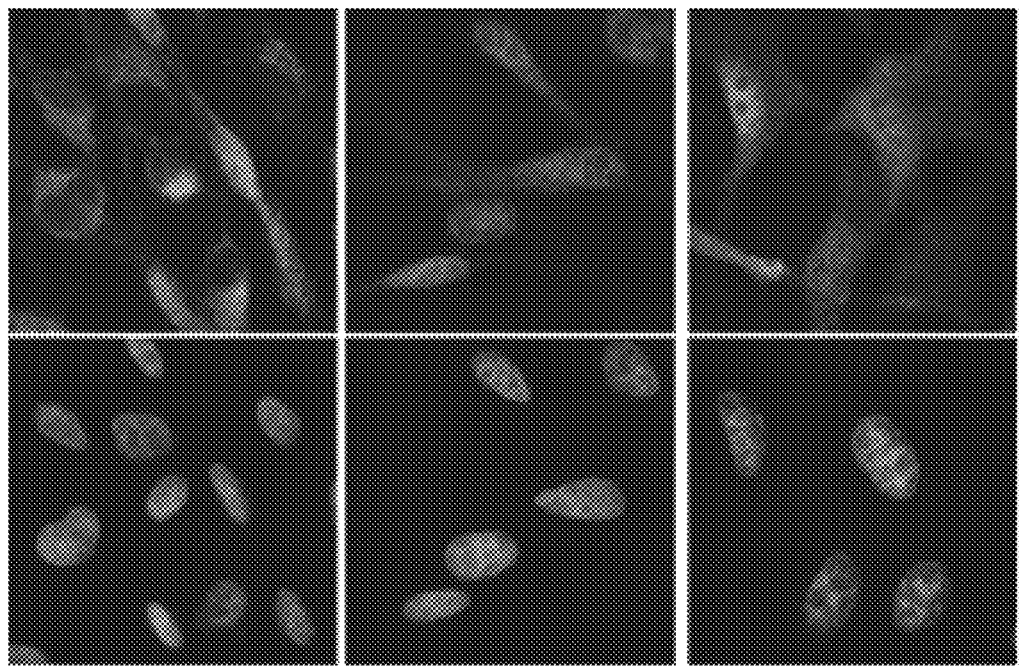

FIG. 16 presents images showing that Compounds D3, D11 and D14 inhibit the stimulated nuclear accumulation of ERK1/2. A2185 cells where serum-starved (0.1%, 16 hours), pretreated with DMSO (0.1%), or Compounds D3, D11 and D14 (1 μM, 2 h), and stimulated with TPA (100 nM, 15 minutes) or left untreated. Nuclear translocation of ERK1/2 was detected by immunostaining with αERK2 (C-14) antibodies and DAPI.

Figure 17:
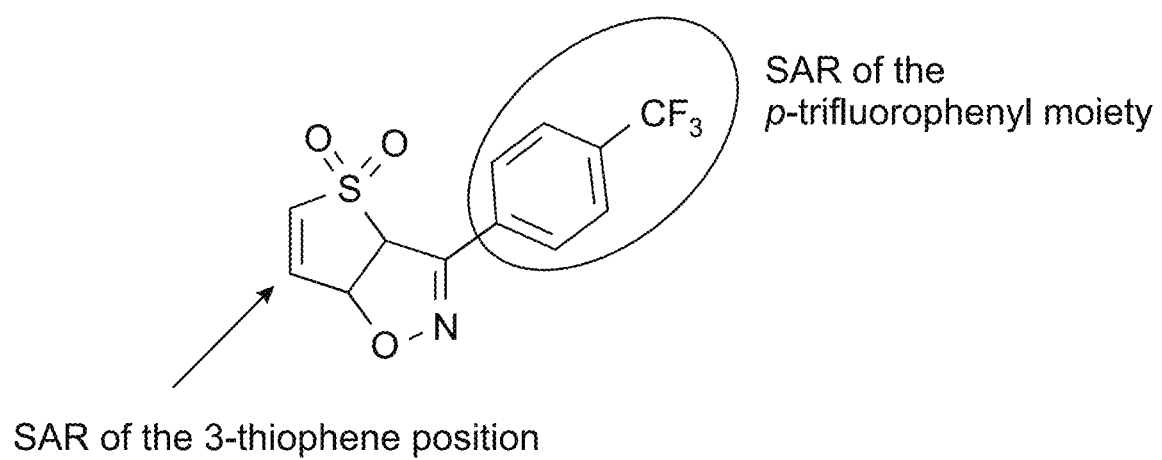

FIG. 17 presents modifications of the structure of Compound C17 for obtaining compounds (for structure activity relationship studies) according to some embodiments of the invention.

DESCRIPTION OF SPECIFIC EMBODIMENTS OF THE INVENTION

The present invention, in some embodiments thereof, relates to therapy, more particularly, but not exclusively, to compounds that inhibit ERK1/2 nuclear translocation and to uses thereof in treating proliferative diseases and disorders such as cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for compounds suitable for modulating ERK1/2 activity, and especially ERK1/2 activity mediated by nuclear translocation of ERK1/2, as well as treating conditions associated with the biological activity of such ERK1/2 activity, the present inventors have searched for small molecules which bind the interface between the kinase and kinase insert domain of ERK1/2, confirmed that such small molecules inhibit ERK1/2 nuclear translocation, and then performed a laborious study of structure-activity relationship in order to identify more potent compounds. Using this laborious process, the present inventors have uncovered that compounds characterized by certain structural features, as detailed herein, were shown to exhibit an ability to inhibit ERK1/2 nuclear translocation and/or reduce cancer cell viability.

Reference is made to FIGS. 1A-2C, which show binding of Compound Z56 to ERK1/2. FIGS. 3-6B show that Compound Z56 inhibits ERK1/2 nuclear translocation, and reduce viability of various types of cancer cell.

FIGS. 7A-8C shows the activity of Compound Z2, an ester analog of Compound Z56. FIGS. 9-11C show that analogs of Compound Z2 exhibited significant activity (including inhibition of ERK1/2 nuclear translocation) when the ester group of Compound Z2 was replaced by an isoxazole-type ring, or when the sulfone-containing ring was substituted. FIGS. 12-16 show that compounds with an isoxazole-type ring exhibit potent and specific activity when substituted by groups such as phenyl or indolyl, and particularly phenyl substituted by chlorine atoms (an electron withdrawing group).

Embodiments of the present invention therefore generally relate to newly designed small molecules and to uses thereof.

Compounds:

The compound, according to any of the embodiments described herein, is represented by Formula I or Formula II:

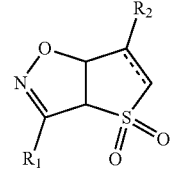

Formula I

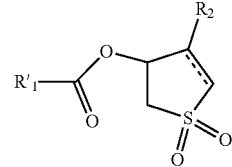

Formula II wherein:
  each dashed line independently represents a saturated or unsaturated bond;
  $R_1$ and $R'_1$ are each independently an aryl or heteroaryl, which is substituted or non-substituted; and
  $R_2$ and $R'_2$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino.

In some of any of the embodiments described herein, $R_1$ and/or $R'_1$ are each independently a substituted or non-substituted aryl or a substituted or non-substituted indolyl (a heteroaryl). In some such embodiments, the dashed line represents an unsaturated bond (e.g., wherein $R_2$ is hydrogen), or the dashed line represents an unsaturated bond and $R_2$ and/or $R'_2$ are halo or O-carboxy (according to any of the respective embodiments described herein).

A substituted or non-substituted indol-3-yl is a non-limiting example of a suitable indolyl. D14 (as described in the Examples section herein) is an exemplary compound comprising an indol-3-yl.

A phenyl (substituted or non-substituted) is a non-limiting example of a suitable aryl. In some embodiments, the phenyl is substituted at a para position and/or one or more meta position thereof, for example, by one or more electron withdrawing groups (according to any of the respective embodiments described herein). In some embodiments, the phenyl is non-substituted at an ortho position thereof, and optionally non-substituted at both ortho positions thereof. 3,4-Dichlorophenyl and 3,5-dichlorophenyl are exemplary substituted phenyl groups which are substituted at a meta or para position (and not at an ortho position).

D3 and D11 (as described in the Examples section herein) are exemplary compounds comprising a chloro-substituted phenyl group.

Examples of suitable substituents for an aryl or heteroaryl described herein (e.g., represented by $R_1$ and/or $R'_1$) include, without limitation, alkyl (e.g., $C_{1-4}$-alkyl), alkoxy (e.g., $C_{1-4}$-alkoxy), halo (e.g., fluoro, chloro, bromo), hydroxy and nitro.

In some of any of the embodiments described herein, an aryl or heteroaryl described herein (e.g., represented by $R_1$ and/or $R'_1$) is substituted by one or more electron withdrawing groups, for example, by at least two (e.g., 2 or 3) electron withdrawing groups.

Examples of suitable electron withdrawing groups include, without limitation, halo, cyano, carbonyl, nitro and haloalkyl (e.g., trifluoromethyl). In some embodiments, the electron withdrawing group(s) comprises halo, for example, chloro or bromo. Chloro is an exemplary electron withdrawing group.

In some of any of the respective embodiments described herein, at least one electron withdrawing group is a halo at a meta position of a phenyl group.

In some of any of the embodiments described herein, when $R_2$ is hydrogen, the adjacent dashed line (in Formula I) represents an unsaturated bond, and when $R'_2$ is hydrogen, the adjacent dashed line (in Formula II) represents an unsaturated bond.

In some of any of the embodiments described herein, $R_2$ and/or $R'_2$ are each independently hydrogen, halo or O-carboxy.

In some embodiments, $R_2$ and/or $R'_2$ are halo or O-carboxy, for example, bromo, chloro or acetoxy. In some such embodiments, the adjacent dashed line represents a saturated bond.

In some embodiments, $R_2$ and/or $R'_2$ are hydrogen. In some such embodiments, the adjacent dashed line represents an unsaturated bond.

In some of any of the embodiments described herein, the compound has Formula I, according to any of the respective embodiments described herein. In some such embodiments, the dashed line represents an unsaturated bond (e.g., wherein $R_2$ is hydrogen), or the dashed line represents an unsaturated bond and $R_2$ and/or $R'_2$ are halo or O-carboxy (according to any of the respective embodiments described herein).

In some of any of the embodiments described herein, the compound has Formula II, according to any of the respective embodiments described herein. In some such embodiments, the dashed line represents an unsaturated bond (e.g., wherein $R_2$ is hydrogen), or the dashed line represents an unsaturated bond and $R_2$ and/or $R'_2$ are halo or O-carboxy (according to any of the respective embodiments described herein).

Without being bound by any particular theory, it is believed that molecules of Formulas I and II tend to adopt a conformation particularly suitable for binding to ERK1 and/or ERK2 in a manner which inhibits nuclear translocation, for example, by binding to (or in proximity to) the insert domain (which may hinder the conformational change needed to expose the nuclear translocation signal) and/or by binding to the region of interaction with importin7 (thus competing with importin7). It is further believed that a particularly suitable conformation of Formulas I and II includes a considerable degree of planarity, for example, substantial co-planarity of $R_1$, and the linker (the isoxazole ring of Formula I of carboxylate of Formula II), and/or the sulfone-containing ring.

In some of any of the embodiments described herein relating to Formula I, $R_1$ is not phenyl (i.e., non-substituted phenyl), 2,4,6-trimethylphenyl, 4-trifluoromethylphenyl, 4-chlorophenyl or 2,6-dichlorophenyl.

For convenience, Formula I in which certain species are explicitly excluded from the definition of $R_1$ is also referred to herein as "Formula I*", which merely indicates particular embodiments of Formula I. Thus, all embodiments described herein relating to Formula I also apply to embodiments of Formula I*, unless explicitly excluded from embodiments of Formula I*.

In some of any of the embodiments described herein relating to Formula I*, $R_1$ is not non-substituted phenyl or phenyl substituted by chloro, methyl (—$CH_3$) or trifluoromethyl (—$CF_3$). In some embodiments, $R_1$ is not non-substituted phenyl or phenyl substituted by halo, non-substituted alkyl or haloalkyl. In some embodiments, $R_1$ is not non-substituted phenyl or phenyl substituted by halo or alkyl (i.e., substituted or non-substituted alkyl).

As used herein throughout, the term "alkyl" refers to any saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted.

When substituted, the substituent group can be, for example, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino, as these terms are defined herein.

Herein, the term "alkenyl" describes an unsaturated aliphatic hydrocarbon comprise at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or non-substituted. Substituted alkenyl may have one or more substituents, whereby each substituent group can independently be, for example, alkynyl, cycloalkyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino.

Herein, the term "alkynyl" describes an unsaturated aliphatic hydrocarbon comprise at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or non-substituted. Substituted alkynyl may have one or more substituents, whereby each substituent group can independently be, for example, cycloalkyl, alkenyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino.

A "cycloalkyl" group refers to a saturated on unsaturated all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino, as these terms are defined herein. When a cycloalkyl group is unsaturated, it may comprise at least one carbon-carbon double bond and/or at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino, as these terms are defined herein. Representative examples are piperidine, piperazine, tetrahydrofuran, tetrahydropyran, morpholine and the like.

Herein, the terms "amine" and "amino" each refer to either a —NR'R" group or a —N$^+$R'R"R'" group, wherein R', R" and R'" are each hydrogen or a substituted or non-substituted alkyl, alkenyl, alkynyl, cycloalkyl, heteroalicyclic (linked to amine nitrogen via a ring carbon thereof), aryl, or heteroaryl (linked to amine nitrogen via a ring carbon thereof), as defined herein. Optionally, R', R" and R'" are hydrogen or alkyl comprising 1 to 4 carbon atoms. Optionally, R' and R" (and R'", if present) are hydrogen. When substituted, the carbon atom of an R', R" or R'" hydrocarbon moiety which is bound to the nitrogen atom of the amine is preferably not substituted by oxo, such that R', R" and R'" are not (for example) carbonyl, C-carboxy or amide, as these groups are defined herein, unless indicated otherwise.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "hydroxy" group refers to a —OH group.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is defined as hereinabove.

A "thiocarbonyl" group refers to a —C(=S)—R' group, where R' is as defined herein.

A "carboxyl", "carboxylic" or "carboxylate" refers to both "C-carboxy" and O-carboxy".

A "C-carboxy" group refers to a —C(=O)—O—R' groups, where R' is as defined herein.

An "O-carboxy" group refers to an R'C(=O)—O— group, where R' is as defined herein.

A "carboxylic acid" refers to a —C(=O)OH group, including the deprotonated ionic form and salts thereof.

An "oxo" group refers to a =O group.

A "thiocarboxy" or "thiocarboxylate" group refers to both —C(=S)—O—R' and —O—C(=S)R' groups.

A "halo" group refers to fluorine, chlorine, bromine or iodine.

A "haloalkyl" group refers to an alkyl group substituted by one or more halo groups, as defined herein.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A "C-amido" group refers to a —C(=O)—NR'R" group, where each of R' and R" is as defined herein.

An "N-amido" group refers to an R'C(=O)—NR"— group, where each of R' and R" is as defined herein.

A "urea group" refers to an —N(R')—C(=O)—NR"R'" group, where each of R', R" and R" is as defined herein.

A "thiourea group" refers to a —N(R')—C(=S)—NR"R'" group, where each of R', R" and R" is as defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The term "phosphinyl" describes a —PR'R" group, with each of R' and R" as defined hereinabove.

The term "hydrazine" describes a —NR'—NR"R'" group, with R', R", and R'" as defined herein.

As used herein, the term "hydrazide" describes a —C(=O)—NR'—NR"R'" group, where R', R" and R'" are as defined herein.

As used herein, the term "thiohydrazide" describes a —C(=S)—NR'—NR"R'" group, where R', R" and R'" are as defined herein.

A "guanidinyl" group refers to an —RaNC(=NRd)-NRbRc group, where each of Ra, Rb, Rc and Rd can be as defined herein for R' and R".

A "guanyl" or "guanine" group refers to an RaRbNC(=NRd)- group, where Ra, Rb and Rd are as defined herein.

Applications:

According to an aspect of some embodiments of the invention, there is provided a compound according to any of the respective embodiments described herein is for use in treating a disease or disorder associated with nuclear translocation of ERK1/2.

According to an aspect of some embodiments of the invention, there is provided a use of a compound according to any of the respective embodiments described herein in the manufacture of a medicament for treating a disease or disorder associated with nuclear translocation of ERK1/2.

According to an aspect of some embodiments of the invention, there is provided a method of treating a disease or disorder associated with nuclear translocation of ERK1/2 in a subject in need thereof, the method comprising administering to the subject a compound according to any of the respective embodiments described herein.

In some of any of the embodiments described herein relating to a disease or disorder associated with nuclear translocation of ERK1/2, according to any of the aspects described herein, the disease or disorder is a proliferative disease or disorder, for example, cancer.

The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor that is not self-limited in its growth, is capable of invading into adjacent tissues, and may be capable of spreading to distant tissues (metastasizing). The term "benign tumor" describes a tumor which is not malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

The cancer may be, for example, a carcinoma, a sarcoma, a blastoma, or germ cell tumor. Carcinomas include, without limitation, adenocarcinomas (e.g., small cell lung cancer, kidney, uterus, prostate, bladder, ovary and/or colon adenocarcinoma) and epithelial carcinomas.

Examples of cancers include, without limitation, bladder cancer, bone cancer, brain cancer, breast cancer, cervical cancer, colorectal cancer, dysgerminoma (testicular or ovarian), endometrial cancer, esophageal cancer, Ewing's tumor, extraskeletal myxoid chondrosarcoma, head & neck cancer, leukemia, liposarcoma, liver cancer, lung cancer, lymphoma, melanoma, myeloma, myxoid sarcoma, neuroblastoma, non-melanoma skin cancer, ovarian cancer, pancreatic cancer, prostate cancer, renal cancer, retinoblastoma, rhabdomyosarcoma, stomach cancer, synovial sarcoma, testis cancer, thyroid cancer, uterine cancer and Wilms' tumor.

Examples of benign tumors include, without limitation, lipomas, chondromas, adenomas, teratomas, and hamartomas.

In some of any of the respective embodiments described herein, the cancer to be treated is a breast cancer, cervical cancer, colorectal cancer, hairy cell leukemia, melanoma, non-small-cell lung cancer, pancreatic cancer, papillary thyroid cancer, and/or prostate cancer. Melanoma and pancreatic cancer are exemplary treatable cancers.

In some of any of the respective embodiments described herein, the proliferative disease or disorder (according to any of the respective embodiments described herein) is associated with a mutation of a protein, such as NF1, Ras, Raf, MEK1/2 and/or ERK1/2. Examples of such mutations include, without limitation, B-Raf mutations (e.g., V600E and V600K mutations of B-Raf), which are associated, for example, with many cases of colorectal cancer, hairy cell leukemia, melanoma, non-small-cell lung cancer, and papillary thyroid cancer.

The compounds of the present invention may optionally be administered in conjunction with other drugs, including other anti-cancer and/or anti-proliferative agents suitable for treating the condition afflicting the subject. Such combinations are known in the art.

For example, the treatment of cancer by a compound according to any of the embodiments described herein may optionally be performed in combination with any suitable treatment known in the art for cancer, for example, chemotherapy, radiotherapy, phototherapy and/or photodynamic therapy, surgery, nutritional therapy, ablative therapy, combined radiotherapy and chemotherapy, brachiotherapy, proton beam therapy, immunotherapy, cellular therapy and photon beam radiosurgical therapy.

In some of any of the embodiments described herein relating to treatment, the treatment further comprises administration of at least one additional agent capable of inhibiting ERK1/2 signaling, such as a Raf inhibitor (e.g., a B-Raf inhibitor) and/or a MEK inhibitor.

Examples of Raf inhibitors include, without limitation, GDC-0879, PLX-4720, dabrafenib, encorafenib, sorafenib, and vemurafenib.

Examples of MEK inhibitors include, without limitation, CI-1040, PD-325901, TAK-733, binimetinib, cobimetinib, selumetinib, and trametinib.

It is expected that during the life of a patent maturing from this application many relevant agents capable of inhibiting ERK1/2 signaling will be developed, and the scope of the terms "additional agent", "Raf inhibitor" and MEK inhibitor" is intended to include all such new technologies a priori.

Alternative or additional chemotherapeutic drugs (e.g., anti-cancer drugs) that may optionally be co-administered with compounds of the invention include, but are not limited to acivicin, aclarubicin, acodazole, acronine, adozelesin, aldesleukin, altretamine, ambomycin, ametantrone, aminoglutethimide, amsacrine, anastrozole, anthramycin, asparaginase, asperlin, azacitidine, azetepa, azotomycin, batimastat, benzodepa, bicalutamide, bisantrene, bisnafide, bizelesin, bleomycin, brequinar, bropirimine, busulfan, cactinomycin, calusterone, caracemide, carbetimer, carboplatin, carmustine, carubicin, carzelesin, cedefingol, chlorambucil, cirolemycin, cisplatin, cladribine, crisnatol, cyclophosphamide, cytarabine, dacarbazine, dactinomycin, daunorubicin, decitabine, dexormaplatin, dezaguanine, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, gemcitabine, hydroxyurea, idarubicin, ifosfamide, ilmofosine, interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine, megestrol, melengestrol, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nocodazole, nogalamycin, ormaplatin, oxisuran, paclitaxel, pegaspargase, peliomycin, pentamustine, peplomycin, perfosfamide, pipobroman, piposulfan, piroxantrone, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine, vindesine, vinepidine, vinglycinate, vinleurosine, vinorelbine, vinrosidine, vinzolidine, vorozole, zeniplatin, zinostatin, zorubicin, and any pharmaceutically acceptable salts thereof.

According to an aspect of some embodiments described herein, there is provided a method of inhibiting nuclear translocation of ERK1/2 in a cell, the method comprising contacting the cell with a compound represented by Formula I or Formula II, according to any of the respective embodiments described herein. The method may optionally be effected in vivo (e.g., by administering the compound to a subject in need thereof) or ex vivo.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Pharmaceutical Compositions:

The active agent(s) (e.g., compounds of Formula I or II and/or co-administered agents) of any of the embodiments of the invention described herein can be administered to a subject per se, or in a pharmaceutical composition where it is mixed with suitable carriers or excipients.

As used herein a "pharmaceutical composition" refers to a preparation of one or more of the active agents described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active agent. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences,"

Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Optionally, one may administer the pharmaceutical composition in a local rather than systemic manner, for example, via injection of the pharmaceutical composition directly into a tissue region (e.g., region of the vasculature) of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active agents into preparations which, can be used pharmaceutically. Proper formulation is dependent upon the route of administration chosen.

For injection, the active agents the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active agents in admixture with filler such as lactose, binders such as starches, lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active agents for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active agents may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active agents to allow for the preparation of highly concentrated solutions.

Alternatively, the active agent may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active agents are contained in an amount effective to achieve the intended purpose. More specifically, a therapeutically effective amount means an amount of active agent(s) effective to prevent, alleviate or ameliorate a disease or disorder according to any of the respective embodiments described herein (or symptoms associated with such a disease or disorder), or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active agents described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. See e.g., Fingl, et al., 1975, in "The Pharmacological Basis of Therapeutics", Ch. 1 p. 1.

Dosage amount and interval may be adjusted individually to provide levels of the active agent(s) (e.g., in the blood) sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions according to some embodiments of the invention may, if desired, be presented in a pack or dispenser device, such as an FDA approved kit, which may contain one or more unit dosage forms containing the active agent(s). The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation according to the invention formulated in a compatible pharmaceutical carrier may also be prepared, placed in an appropriate container, and labeled for treatment of an indicated condition, as is further detailed above.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

A/G agarose beads (Protein A/G PLUS-agarose beads) were obtained from were obtained from Santa Cruz Biotechnology.

Bovine serum albumin (BSA) was obtained from MP Biomedical.

Compound C1 (cat. #IBS-L0035725) was obtained from Alinda (Moscow, Russia).

Compounds C2 (cat. #STT-00010741), C3 (cat. #SST-00205103), C4 (cat. #STT-00204845), C5 (cat. #STT-00129459), C6 (cat. #BBS-00005035), C8 (cat. #STT-00205031) and C11 (cat. #STT-00205066) were obtained from Innovapharm (Kiev, Ukraine).

Compound C12 (cat. #IBS-L0034848) was obtained from Alinda.

Compounds C14 (cat. #Z131367102), C15 (cat. #Z1357540303) and C16 (cat. #Z954576432) were obtained from Enamine (Kiev, Ukraine).

Compound C17 (cat. #STT-00191806) was obtained from Innovapharm.

Compound C19 (cat. #Z57036728) was obtained from Enamine.

Compounds C20 (cat. #BBS-00005047), C21 (cat. #BBS-00005048), C22 (cat. #SST-00293022) and C23 (cat. #STT-00191808) were obtained from Innovapharm.

Compound C31 (cat. #Z1357535933) and C32 (cat. #Z1255131651) were obtained from Enamine. 4,6-Diamino-2-phenylindole (DAPI) was obtained from Sigma Aldrich.

Epidermal growth factor (EGF) was obtained from Sigma Aldrich.

PD184352 was obtained from Sigma Aldrich.

PLX4032 was obtained from Selleck Chemicals (Huston, TX).

Poly-L-Lysine (PLL) was obtained from Sigma Aldrich.

Tetradecanoyl phorbol acetate (TPA) was obtained from Sigma Aldrich.

Trametinib was obtained from Selleck Chemicals.

Compounds Z1 (cat. #Amb114597), Z2 (cat. #Amb756834) and Z3 (cat. #Amb2548610) were obtained from Ambinter (Orleans, France).

Compound Z56 (cat. #Z56764746) was obtained from Enamine.

Antibodies:

Anti-general Elk1 (I-20; gElk1, dilution 1:1000), anti-phosphorylated Elk1 (B-4, S383; pElk1, 1:1000), anti-general RSK1 (C-21; 1:4000), anti-phosphorylated RSK1/2 (T359, S381; 1:2000), anti-phosphorylated cMyc (T58, S62; 1:1000), anti-general PEA-15 (H-3; 1:1000), anti-general cFos (H-125; 1:1000), anti-general ERK1 (C-16; 1:200 immunofluorescence IF), anti-general ERK2 (C-14; 1:200 IF), anti-general GAPDH (FL-335; 1:1000) and normal rabbit IgG antibodies were obtained from Santa Cruz Biotechnology.

Anti-phosphorylated Akt (S473; 1:1000), anti-general CyclinD1 (92G2, 1:1000) and anti-PARP (46D11, 1:1000) antibodies were obtained from Cell Signaling Technology (Beverly, MA).

Anti-Importin7 (1:1000) antibodies were obtained from Abnova (Taiwan).

Anti-phosphorylated ERK1/2 (p(TEY)ERK1/2; 1:20000), anti-general ERK1/2 (1:20000), anti-general ERK1 c-terminus (for co-IP) and anti-general Akt1 (1:10000) antibodies were obtained from Sigma.

Anti-phosphorylated cFos (T325, 1:1000) and anti-general Sprouty2 (amino-terminal, 1:1000) antibodies were obtained from Abcam (Cambridge, UK).

Anti-p(SPS)ERK1/2 (1:500) antibodies were obtained from the Biological Service Unit of the Weizmann Institute of Science (Rehovot, Israel).

Secondary antibodies with conjugated fluorescent labels were obtained from Jackson ImmunoResearch (West Grove, PA). Secondary antibodies conjugated to horseradish peroxidase (HRP) or alkaline phosphatase (AP) (Simple Stained Max) were obtained from Nichirei Biosciences (Japan).

Peptides:

EPE peptide: A peptide with the amino acid sequence GQLNHILGILGEPEQEDL (SEQ ID NO: 1) was conjugated at its N-terminus to myristic acid (according to procedures described by Nelson et al. [*Biochemistry* 2007, 46:14771-14781]) and C-terminal amidated. Scramble (Scr) peptide, used as a control peptide, was prepared as described hereinabove, except that the amino acid sequence was GNILSQELPHSGDLQIGL (SEQ ID NO: 2). The peptides were obtained from GenScript (China) at >85% purity and stored at 100 mM in DMSO at −20° C.

Buffers:

Buffer A: 50 mM β-glycerophosphate (pH 7.3), 1.5 mM EGTA, 1 mM EDTA, 1 mM dithiothreitol, and 0.1 mM sodium vanadate.

Buffer H: 50 mM β-glycerophosphate (pH 7.3), 1.5 mM EGTA, 1 mM EDTA, 0.1 mM sodium vanadate, 1 mM DTT, 1 mM benzamidine, 10 µg/ml aprotinin, 10 µg/ml leupeptin, 2 µg/ml pepstatin A.

Radioimmuno-protein assay (RIPA) buffer: 137 mM NaCl, 20 mM Tris (pH 7.4), 10% glycerol, 1% Triton X-100, 0.5% deoxycholate, 0.1% SDS (sodium dodecyl sulfate), 2 mM EDTA, 1 mM phenylmethylsulfonyl fluoride (PMSF), 20 µM leupeptin.

Sample buffer 4x: 200 mM Tris (pH 6.8), 40% glycerol, 8% SDS, 100 mM dithiothreitol, 0.2% bromophenol blue.

Sample buffer 2x: 2.5% SDS, 25% glycerol, 125 mM Tris Cl pH 6.8, 4% v/v β-mercaptoethanol. 0.01% bromophenol blue.

Co—IP wash buffer: 50 mM β-glycerophosphate (pH 7.3), 1.5 mM EGTA, 1 mM EDTA, 1 mM dithiothreitol, 0.1 mM sodium vanadate and 50 mM NaCl.

Cells:

HeLa (derived from cervical cancer), MDA-MB-231 (Ras-transformed breast cancer), PC-3 (prostate cancer) and MCF7 (breast cancer) cells were obtained from ATCC (Manassas, VA), and were grown in either Dulbecco's modified Eagle's medium (DMEM) or Roswell Park Memorial Institute medium (RPMI). All media were supplemented with 10% fetal calf serum (FCS).

HCT-116 (colon cancer) cells were obtained from the NCI.

Low-passage (<10) primary melanoma cells with BRAF mutation (A2185, A2352, A2024), low-passage vemurafenib-resistant melanoma cells from patients (A4132 and A4168), as well as immortalized non-transformed breast cells (HB2) were obtained from the Ella Institute, Sheba Medical Center, Israel. LOX-IMVI cells, an established melanoma cell line carrying BRAF mutation, were obtained from ATCC. The melanoma cells were grown in RPMI with 10% FCS (fetal calf serum). HB2 cells were grown in the same medium with 10 µg/ml insulin and 0.5 µg/ml hydrocortisone. A4132 and A4168 cells were grown in RPMI with 15% FCS supplemented with 25 mM HEPES and 1 mM Na-pyruvate.

Pancreatic cancer cell lines (Ras-transformed) Panc-1, AsPC-1, CFPAC-1, MIA PaCa-2, Capan-1, Capan-2, and (Ras-wildtype) BxPC-3 were obtained from commercial suppliers. Panc-1 and MIA PaCa-2 cells were grown in DMEM medium, BxPC-3 and AsPC-1 cells were grown in RPMI medium, CFPAC-1 and Capan-1 cells were grown in IMDM medium, and Capan-2 cells were grown in McCoy's 5A medium. All media were supplemented with 10% FCS (fetal calf serum); except Capan-2 cell medium, which was supplemented with 20% FCS. MIA PaCa-2 cell medium was supplemented additionally with 2.5% horse serum. All media above were supplemented with 2 mM L-glutamine and 1% Pen/Strep.

All cells were maintained at 37° C. in a humidified atmosphere of 95% air and 5% $CO_2$.

Determination of Protein Localization by Fluorescence Microscopy:

Indicated cells were seeded on coverslips (coated with 0.001% w/v poly-L-lysine or not, depending on the cell line) at 50% confluency. After the indicated treatment, cells were fixed in 4% paraformaldehyde/PBS for 20 minutes on an ice surface, permeabilized with 0.1% Triton X-100/PBS for 5 minutes at 23° C., then blocked in 2% BSA/PBS for 30 minutes at 23° C. The fixed cells were sequentially incubated with appropriate antibodies (in 2% BSA/PBS, 1.5 hour), washed 3 times with $PBS^{-/-}$, and followed by incubation with either Cy-2-conjugated or rhodamine-conjugated secondary antibodies (1:200) and with DAPI (4,6-diamino-2-phenylindole; 1:100) in 2% BSA/PBS for 45 minutes. Slides were analyzed and photographed by a fluorescence microscope (Olympus BX51, ×40). Background correction, and contrast adjustment of raw data images were performed using Photoshop (Adobe, CA, USA).

Preparation of Cellular Extracts and Western Blotting:

Cells were grown to 70% confluence and serum starved (0.1% FCS, 16 hours). After treatments, cells were rinsed twice with ice-cold PBS-/- and scraped into RIPA buffer. The extracts were centrifuged (15000 rotations per minute, 15 minutes, 4° C.), and the supernatants re-suspended and boiled for 5 minutes in sample buffer 4× (1:4). The samples were then subjected to 12% SDS-PAGE and Western blotting with the appropriate antibodies. The blots were developed with AP or HRP-conjugated anti-mouse or anti-rabbit antibodies.

For tumor tissue cells, media was collected and floating cells where pelleted (8000 rotations per minute, 1 minute, 4° C.) and lysed in Sample buffer 2×. In parallel, adherent cells were scraped into Sample buffer 2×, and combined with pelleted cells. The extracts were sonicated (50 W, 2×7 seconds), incubated on ice for 15 minutes, and boiled for 5 minutes. The samples were then subjected to 10% SDS-PAGE and Western blotting with the appropriate antibodies. The blots were developed with HRP-conjugated anti-mouse or anti-rabbit antibodies, using SuperSignal West Pico Chemiluminescent Substrate® from Thermo Scientific (Waltham, MA).

Quantification of blots was done using ImageJ or Image Lab software (BioRad).

Co-Immunoprecipitation (CoIP) Assay:

Cells were grown to 70% confluence and serum starved (0.1% FCS, 16 hours). After the indicated treatments, cells were rinsed twice with ice-cold PBS-/- and once in buffer A, and then scraped into buffer H on an ice surface. The extracts were sonicated (50 W, 2×7 seconds), centrifuged (15000 rotations per minute, 15 minutes, 4° C.), and incubated (2 hours, 4° C.) with the appropriate antibodies pre-conjugated to A/G beads (2 hours, 23° C.). Subsequently, the beads were washed once with buffer H and twice with co-IP washing buffer, re-suspended in sample buffer 4× (1:4), and boiled for 5 minutes. Lysates were subjected to western blot analysis with appropriate antibodies. The blots were developed with AP or HRP-conjugated anti-mouse or anti-rabbit antibodies. Quantification of blots was done using ImageJ or Image Lab software (BioRad).

Viability Assay:

Cells were seeded at low confluence into 24, 48 or 96-well plates in complete medium. After 24 hours, medium was replaced by 1% FCS (fetal calf serum) containing appropriate treatments. Fresh medium containing the same agents was replaced every day. After 72 or 96 hours of treatment, cells were fixed with 4% formaldehyde overnight at 23° C., washed once with 0.1 M borate buffer (pH 8.5) for 10 minutes, and stained with of 1% methylene blue in 0.1 M borate buffer (pH 8.5) for 30 minutes. Excess stain was washed out with distilled water. Color was extracted by adding 0.1 M HCl (3 hours, 23° C.), and absorbance measured at 595 nm in an ELISA reader. For time course experiments, attached cells were fixed and measured at 0, 24, 48, 72 and 96 hours. For dose-response experiments, cells were treated with indicated concentrations of reagent, fixed and stained after 72 hours as above.

Cell Viability ($IC_{50}$) Assay:

Cells were seeded at a density of 4000 cells per well into 96-well plates in complete medium. After 24 hours, medium was replaced by 1% FCS (fetal calf serum) containing appropriate treatments. Fresh medium containing the same agents was replaced every day. After 96 hours, cell viability was assessed using the CellTiter-Glo reagent (Promega; Madison, WI). IC50 values were determined using Graph-Pad Prism.

Statistical Analysis:

Data are expressed as mean±standard error. Statistical evaluation was carried out using functional analysis and Student's t test (two-tailed) to test for differences between the control and experimental results. Values of $p<0.05$ were considered statistically significant. Calculations were done using Microsoft Excel.

Example 1

In Silico Screening for Nuclear Translocation Inhibitor

Stimulation-dependent translocation of ERK1/2 to the nucleus is mediated by recognition of its phosphorylated NTS (nuclear translocation signal) sequence, which is part of the kinase insert domain (KID). Observation of crystallographic structures available in the Protein Data Bank (PDB) shows that in basal state, ERK1/2's KID has a defined shape and is well packed against the kinase domain. In this conformation, the NTS sequence is not accessible.

It was hypothesized that nuclear translocation requires a conformational change of ERK1/2 molecules that results in detachment of the KID from the kinase domain, and therefore, stabilization of the observed conformation by means of a small molecule binding at the interface between the kinase and KID would effectively block ERK1/2 nuclear translocation. Structural information deposited in the PDB was then analyzed in order to seek potential ligand binding sites (druggable cavities) at the interface between the kinase and insert domains.

The Advanced Search tool of the PDB Database (www(dot)rcsb(dot)org) was used to perform a sequence search (BLAST), using the sequence of a reference structure (3W55) as query and an E-Value cutoff of 1E-100. The query returned 53 structures, corresponding to 32 human ERK2 structures (Uniprot code P28482), 20 rat ERK2 structures (Uniprot code P63086) and 1 human ERK1 structure (Uniprot code P27361). All structures were loaded and structurally aligned using the open source molecular visualization software PyMOL. Structures were individually visualized looking for presence of organic molecules. The PDB structure 3QYI was found to present a ligand (3R)-1,1-dioxido-2,3-dihydrothiophen-3-yl benzenesulfonate, which was termed Z56.

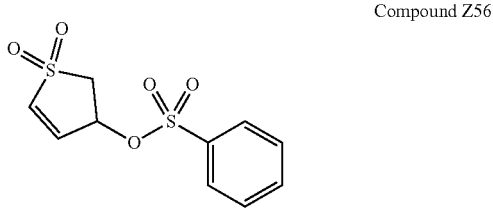 [SMILES: O=S1(=O)C=CC(OS(=O)(=O)c2ccccc2)C1]

Compound Z56

As shown in FIG. 1A, the PDB structure 3QYI shows that Z56 binds to ERK2 between the activation loop and the insert domain, presenting a dual binding mode; and although it interacts mostly with the kinase domain, it also makes stable interactions with the insert domain in both binding modes.

This result suggests that by making contact with the insert domain and the rest of the protein, Z56 might hinder the conformational change needed to expose the NTS, and/or bind to the region of interaction with importin7 and compete for it. Therefore, binding of Z56 to ERK1/2 might reduce ERK1/2 nuclear translocation.

As further shown in FIG. 1A, in binding mode 1 (50% occupancy), the compound does not make contact with the activation loop and makes both hydrophobic and polar contacts (hydrogen bond) with the insert domain. On the other hand, in binding mode 2 (30% occupancy), the compound makes contact with the activation loop, but the contact with the insert domain is minor and only hydrophobic.

These results suggest that although the conformation of binding mode 2 could slightly interfere with the activation of ERK1/2, the binding appears to be too weak to exert changes in ERK1/2 activity; and that binding mode 1 is more likely to hinder the separation of the insert domain compared to binding mode 2.

In order to assess the druggability of the ERK2 binding site of Compound Z56, to identify key interaction points (hot spots) and to obtain information useful for identifying new binding molecules, MDmix simulations (a computational method described in Seco et al. [*J Med Chem* 2009, 52:2363-2371] and Alvarez-Garcia & Barril [*J Med Chem* 2014, 57:8530-8539]) were performed.

As shown in FIG. 1B, the calculated interaction maps show that the binding site of Z56 has a moderate tendency to bind organic molecules; and that binding mode 1 of Z56 overlaps with favorable interaction spots in the calculated map, suggesting that this conformation is the most likely to have inhibitory activity.

However, as further shown therein, additional binding hot spots have been detected in the periphery of Compound Z56 binding site, indicating that it should be possible to increase the binding affinity of a compound by modifications of the structure of Compound Z56 that reach towards those positions.

As further shown in FIG. 1B, the death effector domain of protein PEA-15 interacts with ERK2 at the same binding site of Compound Z56 (PDB code 4IZA).

This result confirms that the interfacial pocket displays affinity for organic molecules, and suggests a functional role for the site. Although, in theory, peptides derived from PEA-15 might also act as inhibitors of translocation, the protein-protein contact area is very small and the expected binding affinity very low.

Taken together, these results indicate that it could be possible to identify new ERK1/2 nuclear translocation inhibitors by designing chemical analogs of Compound Z56 with increased binding affinity.

Example 2

New Binding Modes of Compound Z56 to ERK2

The binding modes of Compound Z56 presented in the PDB structure were further investigated, in order to uncover advantageous chemical modifications to Compound Z56.

As shown in FIG. 2A (left panel), observed electron density is missing for the Compound Z56 and for the activation loop in both the backbone and side chain.

As shown in FIG. 2A (right panel), an electron difference map shows areas where there is more electron density observed than explained by the model (blue mesh) as well as areas where there is less electron density than explained by the model (red mesh).

In addition, the S atoms of Compound Z56 are not identifiable in the model and their position should have been apparent since they are very rich in electrons.

These results indicate that the binding modes present in the PDB structure might be inaccurate and fail to reflect the actual binding mode.

Other possible binding modes were generated using the open source molecular docking software rDock (Ruiz-Carmona et al. [*PLoS Comput Biol* 2014, 10:e1003571]). These binding modes may be at least as valid as the ones depicted in the PDB structure.

Notably, Compound Z56 is a chiral molecule and the commercial form is a racemic mixture. Both binding modes present in the PDB structure correspond to the R enantiomer, although the S enantiomer is equally possible and could be placed in the binding site without difficulties.

As shown in FIG. 2B, three new binding modes of Compound Z56 were generated (binding modes 3-5), in addition to the two binding modes present in the PDB structure 3QYI (binding modes 1 and 2).

Molecular dynamics simulations were then performed in order to investigate the stability of the binding modes in the PDB structure and identify potential alternative binding modes. For each of the abovementioned binding modes 1-5, a minimum of five molecular dynamics simulations (with different initial velocities) were performed, and after 20 ns the simulations were analyzed.

In most cases, the compound moved away from the initial conformation, gradually dissociating from the binding site. This result suggests that the initial configurations do not correspond to a minimum in the free energy landscape.

In a few cases, the compound appeared to adopt a stable binding mode, in which case the simulations were extended to 50 ns, 80 ns and 100 ns. At the end of each stage, the binding mode was examined again and the simulation was extended only if the binding mode remained stable. The aggregated simulation time reached was approximately 1 µsec (>60 GPU days).

As shown in FIG. 2C, two stable new binding modes (referred to as new binding modes 1 and 2) were uncovered by molecular simulations (after 100 ns).

New binding mode 1 appears particularly plausible since the interactions seem stronger and more stable. In both new binding modes, the compound forms simultaneous interactions with the kinase and insert domain, as would be necessary to prevent unfolding of the insert domain.

These results indicate that even though other binding modes may occur, Compound Z56 still binds to ERK1/2 in a manner which would block the nuclear translocation of ERK1/2.

Example 3

Effect of Z56 on ERK1/2 Signaling

In order to experimentally confirm that Compound Z56 inhibits ERK1/2 nuclear translocation, and associated physiological effects, the effect of the nuclear localization of ERK1/2 after stimulation with 100 nM TPA (tetradecanoyl phorbol acetate) for 15 minutes was evaluated in MCF7, A2352, HB2 and HeLa cells, using fluorescent microscopy and fluorescent-labeled anti-ERK2 antibodies, according to procedures described in the Materials and Methods section hereinabove. The effect of Z56 was compared with that of the inhibitory effect of EPE peptide on nuclear translocation of ERK1/2.

As shown in FIG. 3, Compound Z56 considerably reduced the degree of ERK1/2 nuclear localization induced by TPA (quantified as the percentage of cells with nuclear ERK1/2 staining) in all four cell lines examined, with ERK1/2 molecules remaining in the cytoplasm after stimulation. The effect of Compound Z56 was similar to that of the EPE peptide, with both Compound Z56 and EPE peptide resulting in a phenotype similar to the basal state.

The effect of Compound Z56 on the ERK1/2-importin7 interaction was then determined using Western blotting and co-immunoprecipitation, according to procedures described in the Materials and Methods section hereinabove.

As shown in FIG. 4A, pre-incubation of A2352 cells with Compound Z56 for 2 hours inhibited the TPA stimulation-dependent interaction of importin7 with ERK1, as determined by co-immunoprecipitation.

As shown in FIG. 4B, the Compound Z56, similarly to the EPE peptide, did not significantly affect levels of phosphorylated RSK1 (cytoplasmic target of ERK1/2) or of ERK1/2 phosphorylated at the TEY activation loop motif upon TPA stimulation in 4 tested cell lines (including A4168, a resistant primary melanoma cell line), indicating that Compound Z56 does not inhibit the kinase domain activity of ERK1/2 or the ability of ERK1/2 to phosphorylate cytoplasmic targets such as RSK1/2.

As further shown in FIG. 4B, Compound Z56 significantly reduced levels of phosphorylated c-Myc (a nuclear target of ERK1/2) in all 4 tested cell lines upon TPA stimulation and levels of phosphorylated Elk1 (a nuclear target of ERK1/2) in 3 of 4 tested cell lines upon TPA stimulation, indicating that activity of ERK1/2 in the nucleus is inhibited.

As further shown therein, levels of phosphorylation of the NTS of ERK1/2 upon TPA stimulation was slightly reduced by Compound Z56, although this effect varied among different cell types. This result suggests the ability of Compound Z56 to partially stabilize the packed conformation of the insert domain, as suggested by the models.

As shown in FIG. 4C, incubation with Compound Z56 did not significantly change the phosphorylation levels of Akt upon TPA stimulation before or after exposure to Compound Z56, in most of the cell lines examined.

Taken together, the above results indicate that Compound Z56 inhibits ERK1/2 nuclear translocation by a similar mechanism as does the EPE peptide.

In view of the similarities between Compound Z56 inhibition of nuclear translocation and EPE peptide inhibition, the effects of Z56 and EPE peptide on proliferation/viability of a variety of cancer-derived cell lines were compared.

As shown in FIG. 5A, 3 µM of Compound Z56 induced apoptosis in all cell lines in which 10 µM EPE peptide induced apoptosis (HeLa cervical cancer, A2352, A2185, LOX-IMVI, A4132 and Z2024 melanoma, and MDA-MB-231 breast cancer cells), and did not significantly affect proliferation of cell lines whose proliferation was not significantly affected by 10 µM EPE peptide (PC3 prostate cancer, A2058 melanoma and MCF7 breast cancer cells).

As shown in FIG. 5B, the reduction of cell viability by Compound Z56 was dose dependent in cells which are sensitive to EPE peptide, but 10 µM of Compound Z56 also affected some EP peptide-insensitive cells, suggesting possible existence of undesirable off-target effects at higher concentrations.

In view of the above, further experiments with Compound Z56 were conducted at a final concentration of 3 µM.

Example 4

Effect of Compound Z56 on Pancreatic Cancer Cells

Activating mutations in Ras are found in more than 95% of pancreatic cancers where signaling through both Raf and Akt pathway drives cancer progression [Campbell et al., *Cancer Res* 2007, 67:2098-2106]. However, no effective treatments that target this mutant protein have reached the clinic to date, and pancreatic ductal adenocarcinoma remains an almost universally fatal disease [Bryant et al., *Trends Biochem Sci* 2014, 39:91-100]. Therefore, treating these pancreatic cancer cells downstream of Ras, without overactivating the Akt pathway, should be at least partially beneficial. The effect of Compound Z56 (and EPE peptide) on cell viability of Ras-transformed (and Ras-wild type) pancreatic cancer cells was determined, using a variety of cell lines.

As shown in FIG. 6A, 3 µM of Compound Z56 considerably reduced cell proliferation/viability (relative to control) of all 7 tested pancreatic cancer cell lines and induced apoptosis in the Panc-1, MIA PaCa-2, Capan-1 and Capan-2 pancreatic cell lines; whereas 10 µM EPE peptide reduced cell viability and induced apoptosis in only 2 of the 7 tested cell lines (Panc-1 and AsPC-1). Furthermore, the EPE peptide reduced cell proliferation in Ras-wild type BxPC-3 pancreatic cancer cells only by 50% (relative to control), and had no major effect on the proliferation/viability of 4 Ras-transformed pancreatic cell lines (other than Panc-1 and AsPC-1).

These results indicate that targeting the nuclear translocation of ERK1/2 in pancreatic cancer can serve as a general approach to treatment, which is effective for a variety of pancreatic cell types. The lack of response to the EPE peptide in five of the seven cell lines examined suggests that the peptide is more susceptible to degradation and/or secretion/expulsion inside some cells, or that such cells are less permeable to the peptide.

Without being bound to any particular theory, it is believed that Compound Z56 (being a small molecule) is relatively effective (e.g., in comparison to EPE peptide) at penetrating cell membranes and remaining in the cytosol (without being degraded).

The effects of Compound Z56 on the viability of pancreatic cancer cell lines at various times after treatment was compared with those of PLX4032 (a B-Raf inhibitor) and PD184352 (a MEK1/2 inhibitor).

As shown in FIG. 6B, Compound Z56 reduced cell viability by 24 hours of treatment in all 4 tested pancreatic cancer cell lines; whereas PLX4032 had a significant effect on proliferation only in Ras-wild type BxPC-3 cells, and to some extent in Ras-mutated AsPC-1, while not affecting the viability of the other Ras-transformed pancreatic cancer cells. Furthermore, PD184352 reduced the viability in all tested cell lines, but the effect of Compound Z56 was similar to or stronger than that of PD184352.

These results indicate that Compound Z56 is as effective as or even better than clinically used inhibitors of components of the ERK1/2 cascade, in inhibiting proliferation of pancreatic cancer cells.

Example 5

Structure-Activity Relationship Based on Compound Z56

Although Compound Z56 inhibits the nuclear translocation of ERK1/2, its $IC_{50}$ is in the range of 3 µM, which is too high for clinical use. It may also have off-target effects at higher concentrations, and possibly unwanted covalent bonding to proteins, due to the reactivity of its sulfonic ester moiety, which narrow its therapeutic window. Anti-cancer compounds with higher efficacy were sought, in order to develop drugs for clinical use.

In the absence of a defined binding mode, it would be highly challenging to propose precise chemical transformations that might increase the binding affinity or improve the pharmacological profile of Compound Z56. However, the new putative binding modes described hereinabove in Example 2 suggest that it could be possible to introduce two chemical transformations that may be beneficial by avoiding genotoxicity associated with chemical instability of the sulfonic ester moiety (an alkylating agent). One such chemical modification is to change the phenyl group to p-toluyl, as toluene derivatives can be less genotoxic than the corresponding benzene [Glowienke et al., *Mutat Res* 2005, 581: 23-34], and addition of the methyl group in a hydrophobic area may increase binding affinity. Another chemical modification is replacement of the sulfonic ester linker by an ester or sulfonamide linker. For example, the putative binding modes suggested that replacement of an oxygen atom (H-bond acceptor) in the sulfonic ester by —NH—(H-bond donor) could be well tolerated.

The activity of Compound Z56 was compared with that of the structurally related commercially available compounds: Z1 (p-toluene analog of Z56), Z2 (ester analog of Z56) and Z3 (sulfonamide plus p-toluene analog of Z56); the structures of which are presented in FIG. 7A. The effects of the compounds on ERK1/2 nuclear translocation were evaluated in three cell lines (HeLa cells and two melanoma cell lines, A2185 and A2352), by treating the cells with each compound for two hours, and determining nuclear translocation using fluorescent anti-ERK antibodies, according to procedures described hereinabove.

As shown in FIGS. 7B and 7C, Compounds Z1 and Z2 significantly reduced the stimulated nuclear translocation of ERK1/2 in both tested two melanoma cell lines and in HeLa cells, although Compound Z1 exhibited only a partial effect in HeLa cells, whereas the sulfonamide-p-toluene analogue Compound Z3 exhibited no significant effect as an inhibitor of ERK1/2 nuclear translocation in any of the tested cell lines.

The effect of Compound Z56 on cell viability was also compared with that of Compounds Z1, Z2 and Z3 in four cancer lines.

As shown in FIG. 8A, Compounds Z1 and Z2 reduced cell viability by about 60% in 3 or 4 cell lines; whereas Compound Z3 had no significant effect on cell viability.

As shown in FIG. 8B, Compounds Z1 and Z2 reduced cell viability (in A2185 cells) in a dose dependent manner; whereas the dose response curve of Compound Z3 confirmed that Compound Z3 is inactive.

As further shown therein, Compounds Z1 and Z2 appeared somewhat less potent than Compound Z56, although such an apparent loss of potency might be outweighed by a gain in specificity which results in less toxicity and/or activation of off-target pathways.

As shown in FIG. 8C, none of Compounds Z56, Z1, Z2 or Z3 affected phosphorylation of either the activation loop of ERK1/2 or the cytosolic target RSK1/2 in A2185 or HeLa cells.

As further shown therein, Compound Z56 reduced the phosphorylation of the NTS of ERK1/2, and only Compound Z2 exhibited a similar effect in A2185 or HeLa cells. Furthermore, both Compounds Z56 and Z2 reduced the phosphorylation of ERK1/2 nuclear targets, with levels of phosphorylated c-Myc being decreased by Compounds Z56 and Z2 in both cell lines, and levels of phosphorylated Elk1 being decreased significantly by Compounds Z56 and Z2 in the melanoma cell line A2185.

As shown in FIG. 8C, Compound Z1 surprisingly failed to exhibit a detected effect on ERK1/2 targets, suggesting that the compound may be less potent and/or act via unrelated mechanisms.

Based on these results, further studies utilized Compound Z2 as a lead compound for further structure-activity relationship studies and chemical modifications.

Example 6

Structure-Activity Relationship Based on Compound Z2

Although Compound Z2 exhibits some advantages relative to Compound Z56 (as discussed hereinabove), further improved inhibition of ERK1/2 nuclear translocation was sought.

From a medicinal chemistry perspective, Compound Z56 is clearly better than Compound Z2, but the ester link is still prone to hydrolysis and might still be susceptible to chemical modification inside the cell.

A structure-activity relationship (SAR) screening was therefore performed based on Compound Z2, in order to obtain information regarding key features in the molecule that are relevant for its activity as an inhibitor of the nuclear translocation of ERK1/2, which would be helpful to design new chemical entities.

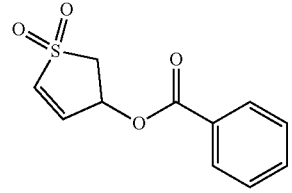 [SMILES: O=C(NC1C=CS(=O)(=O)C1)c1ccccc1]

Compound Z2

For this purpose, a group of 20 commercially available compounds (depicted in Table 1 below) were selected (referred to as "C-compounds"), with the primary aim of detecting more "drug-like" scaffolds rather than a more potent compound. The compounds were tested as racemic mixtures.

As described in FIG. 9 and in Table 1, the selection of compounds was targeted at analyzing six notable sites in the structure of Compound Z2, namely:
  (a) the presence or absence of the double bond in the sulfolene (dihydrothiophene-1,1-dioxide) (site A in FIG. 9);
  (b) substitution at position 3 in the sulfolene ring (site B in FIG. 9);
  (c) replacement of the 5-membered sulfolene ring by a 6-membered ring or no ring (site C in FIG. 9);
  (d) replacement of the ester bond by amide, reverse amide, carbamate, amine, methylene-ether or ether bonds (site D in FIG. 9);
  (e) closing of the ester linker into a isoxazole-type ring (site E in FIG. 9); and
  (f) modification of the benzene moiety (site F in FIG. 9).

The ability of the selected compounds to reduce cell viability of two BRAF melanoma cells (A2185 and A2352) was evaluated. Initially, all compounds were assayed at a relatively high concentration of 10 µM.

TABLE 1

Compounds ("C-compounds") used for structure activity relationship studies, based on chemical modifications of the structure of Compound Z2

| Compound Name | Compound Structure | Type of Primary Modification of Compound Z2 |
|---|---|---|
| C1 | (structure) | Replacement of ester (by amine) |
| C2 | (structure) | Replacement of ester (by amide) |
| C3 | (structure) | Modification of benzene moiety |
| C4 | (structure) | Modification (elimination) of benzene moiety |
| C5 | (structure) | Replacement of ester (by ether) |
| C6 | (structure) | Absence of sulfolene ring double bond |
| C8 | (structure) | Replacement of ester (by methylene ether) |
| C11 | (structure) | Absence of sulfolene ring double bond |
| C12 | (structure) | Replacement of ester (by carbamate) |
| C14 | (structure) | Replacement of ester (by reverse amide) |

TABLE 1-continued

Compounds ("C-compounds") used for structure activity relationship studies, based on chemical modifications of the structure of Compound Z2

| Compound Name | Compound Structure | Type of Primary Modification of Compound Z2 |
|---|---|---|
| C15 | 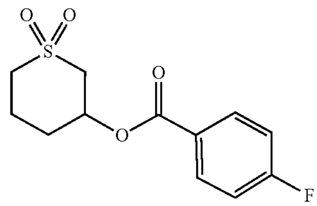 [SMILES: O=C(OC1CCCS(=O)(=O)C1)c1ccc(F)cc1] | Replacement of sulfolene ring (by six-membered sulfone-containing ring) |
| C16 | 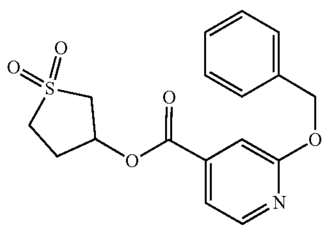 [SMILES: O=C(OC1CCS(=O)(=O)C1)c1ccnc(OCc2ccccc2)c1] | Modification of benzene moiety |
| C17 | 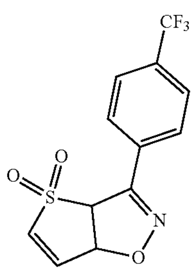 [SMILES: O=S1(=O)C=CC2ON=C(c3ccc(C(F)(F)F)cc3)C21] | Replacement of ester by closed isoxazole-type ring |
| C19 | 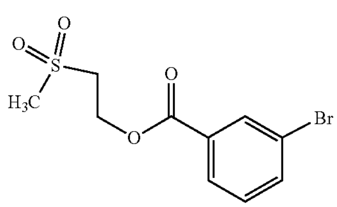 [SMILES: CS(=O)(=O)CCOC(=O)c1cccc(Br)c1] | Replacement of sulfolene ring (by acyclic sulfone) |
| C20 | 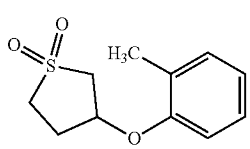 | Replacement of ester (by ether) |
| C21 | 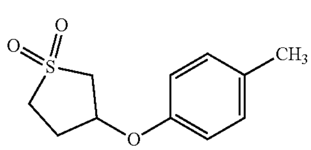 | Replacement of ester (by ether) |
| C22 | 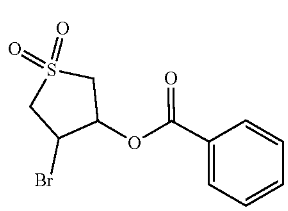 [SMILES: O=C(OC1CS(=O)(=O)CC1Br)c1ccccc1] | Substituted at position 3 of the sulfone-containing ring |
| C23 | 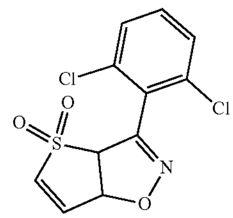 [SMILES: O=S1(=O)C=CC2ON=C(c3c(Cl)cccc3Cl)C21] | Replacement of ester by closed isoxazole-type ring |
| C31 | 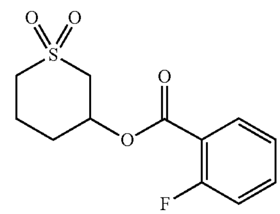 [SMILES: O=C(OC1CCCS(=O)(=O)C1)c1ccccc1F] | Replacement of sulfolene ring (by six-membered sulfone-containing ring) |
| C32 | 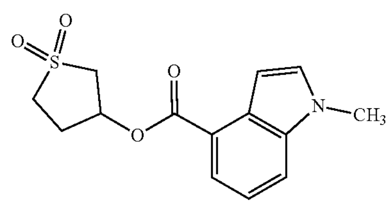 [SMILES: Cn1ccc2c(C(=O)OC3CCS(=O)(=O)C3)cccc21] | Modification of benzene moiety |

As shown in FIG. 10A, at a concentration of 10 μM, Compounds C1, C17, C22 and C23 each exhibited considerable activity, reducing cell viability to below 40%; Compounds C2, C3 and C5 exhibited moderate activity, reducing cell viability to below 80%; and Compounds C4, C6, C8, C11, C12, C14, C15, C16, C19, C20, C21, C31 and C32 did not exhibit significant activity.

The compounds exhibiting the most potent activity (C1, C2, C3, C5, C17, C22 and C23, along with Z56 and Z2) were then tested at a lower concentration of 3 μM in a cell viability assay.

As shown in FIG. 10B, Compound C 17 exhibited a consistently strong anti-viability effect, and Compounds C22 and C23 appeared to be at least as potent as Compound Z2. Furthermore, many of the tested compounds exhibited variable activity (including Compound Z2 in one cell line), indicating that they are somewhat active, but are tested at the beginning of the dose response curve, where minor changes in concentration can change the observed effect to a considerable degree.

In view of the above, Compounds C17, C22 and C23 were subjected to further testing at a range of concentrations.

As shown in FIG. 10C, each of the tested Compounds C17, C22 and C23 reduced the viability of both A2185 and A2352 cells in a dose dependent manner, with Compound C17 exhibiting activity already at a concentration as low as 0.3 μM.

As further shown therein, Compound C17 was as potent in reducing the viability of A2352 cells, which are usually less sensitive to drugs, as reducing the viability of the more sensitive A2185 cells.

The mechanism of action of the compounds that gave the best viability-reducing activity (C17, C22 and C23) was then verified by examining their effects on nuclear translocation of ERK1/2, according to procedures described hereinabove.

As shown in FIGS. 11A-11C, Compounds C17, C22 and C23, as well as Compounds Z56 and Z2 and EPE peptide, each inhibited the nuclear accumulation of ERK1/2 upon TPA stimulation, changing the localization of ERK1/2, as observed by fluorescent microscopy, to a more evenly distributed or even mostly cytosolic phenotype, in both A2185 and A2352 cells.

As further shown in FIGS. 11B and 11C, Compound C17 was more potent than Compounds C22 and C23 (in A2185 cells).

Taken together, the above results (e.g., as shown in FIGS. 10A-10C) indicate the following:

(a) All else being equal, the double bond in the sulfolene (dihydrothiophene-1,1-dioxide) ring appears to be essential for activity (as Compounds C6 and C11 were inactive);

(b) a halogen substituent at the 3-position enhances activity, at least in a sulfolane (tetrahydrothiophene-1,1-dioxide) ring (as Compound C22 was far more active than Compound C6);

(c) replacement of the 5-membered sulfolene ring with a 6-membered ring or no ring results in less active compounds (as Compounds C15, C31 and C19 were inactive);

(d) substitution of the ester group of Compound Z2 by amide (as in Compound C2), methylene ether (as in Compound C8) or carbamate as in Compound C12) resulted in less active compounds; and the lower activity (relative to Compound Z2) of Compounds C1, C20, C21 and C14 suggests that amine, reverse amide and ether groups may less suitable than the ester group of Compound Z2 as a linker (although these compounds present multiple changes relative to Compound Z2, rendering this conclusion less certain);

(e) the directly fused isoxazole-type ring (as in Compound C17) was surprisingly superior to the ester group of Compound Z2 (although Compound C23, which also comprises an isoxazole-type ring, was less active, this appears to be due to the ortho-Cl substituents thereof, which may force the benzene ring out of coplanarity with the 5-membered ring); and (f) the benzene ring tolerated significant substitutions (e.g., as in Compound C3), which suggests it can be further optimized.

Furthermore, the above results show a generally consistent SAR, which provides further evidence (e.g., in addition to results presented in FIGS. 11A-11B) that the observed cellular activity is associated with ERK1/2 binding.

Compound C17 is clearly outstanding, not only due to its high potency ($IC_{50}$ of about 1 µM), but also because its chemical structure is of an uncommon nature (presenting a wide range of potential modified structures which have hitherto been untested), does not present any obvious ADME-Tox issue and optimization around the benzene ring is expected to allow for a significant gain in potency.

Compound C17 was previously reported as a hit in a high-throughput screening for anti-tubercular activity (via an unknown mechanism), without presenting cytotoxic activity in mammalian cells [Ananthan et al., Tuberculosis (Edinb) 2009, 89:334-353].

Example 7

Structure-Activity Relationship Based on Compound C17

In view of the results presented in Example 6, Compound C17 was utilized as a lead compound for further structure-activity relationship studies and chemical modifications. As further discussed in Example 6, SAR analysis of Compound Z2 indicates that the benzene ring moiety therein tolerates large substitutions, suggesting it can be significantly further optimized. A group of novel compounds (referred to herein as "D-compounds") were designed and prepared, based on modification of the 4-trifluoromethylphenyl moiety of Compound C17.

A general chemical synthetic route was used based on a one step 1,3-cycloaddition reaction, as depicted in Scheme 1:

Scheme 1

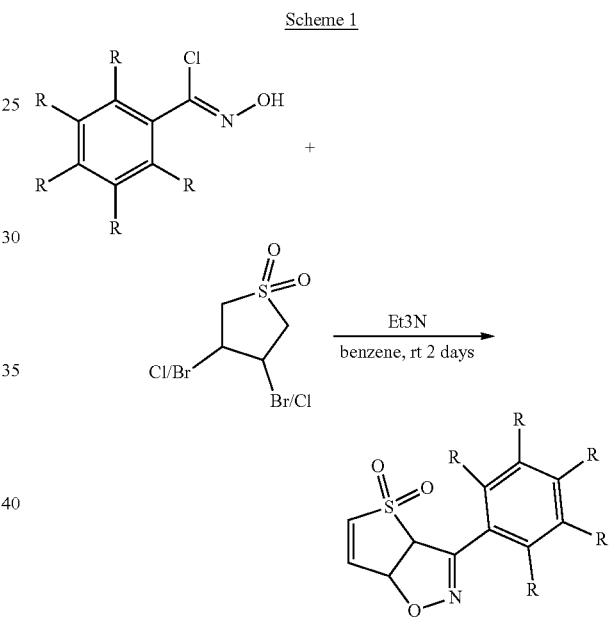

Sulfolane, optionally substituted at the 3 and 4 positions by chlorine or bromine (e.g., 3,4-dibromosulbolane) is reacted with an equimolar amount of an N-hydroxybenzimidoyl chloride, or an analog thereof, wherein the phenyl moiety is replaced by a different aromatic moiety (not shown in Scheme 1 for the sake of simplicity), for two days at room temperature in benzene and triethylamine. The reaction is regioselective (99% regioisomer of interest), and the product is purified by crystallization with ethanol.

Based on the above general procedure, the 16 novel compounds depicted in Table 2 below were prepared.

As shown in FIG. 12 and in Table 2, the compounds depicted in Table 2 differ from Compound C17 in having a group other than trifluoromethyl at the para-position of the phenyl (site A in FIG. 12); in that the phenyl is meta-substituted (site B in FIG. 12); in having a group other than trifluoromethyl at the para-position of the phenyl and in that the phenyl is meta-substituted (C in FIG. 12); in that the phenyl has a second meta-substituent (site D in FIG. 12); or in having an aromatic moiety other than phenyl (site E in FIG. 12).

Substituted phenyl groups in the prepared compounds were substituted only at para- and/or meta-positions, as ortho-substitution tended to reduce activity in results presented hereinabove.

TABLE 2

Compounds ("D-compounds") used for structure activity relationship studies, based on chemical modifications of the structure of Compound C17

| Compound Name | Compound Structure | Type of Primary Modification of Compound C17 |
|---|---|---|
| D1 | | Replacement of trifluoromethyl substituent at para position of phenyl |
| D2 | | Replacement of trifluoromethyl substituent at para position of phenyl |
| D3 | | Phenyl substituents at both meta positions |
| D4 | | Phenyl substituent at meta position and replacement of trifluoromethyl substituent at para position |
| D6 | | Phenyl substituent at meta position |
| D7 | 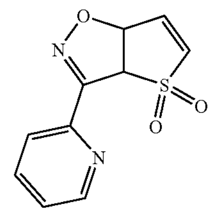 [SMILES: O=S1(=O)C=CC2ON=C(c3ccccn3)C21] | Replacement of phenyl with heteroaryl (pyridin-2-yl) |
| D8 | 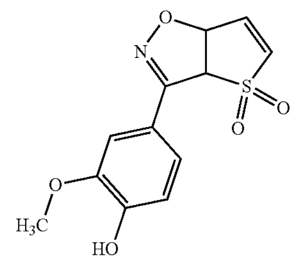 [SMILES: COc1cc(C2=NOC3C=CS(=O)(=O)C23)ccc1O] | Phenyl substituent at meta position and replacement of trifluoromethyl substituent at para position |
| D9 | 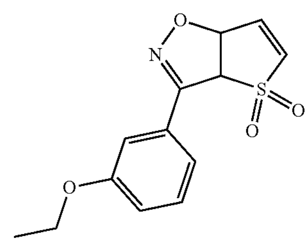 [SMILES: CCOc1cccc(C2=NOC3C=CS(=O)(=O)C23)c1] | Phenyl substituent at meta position |
| D10 | 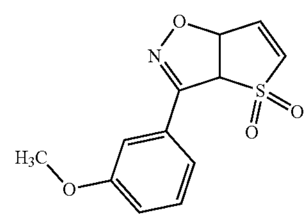 [SMILES: COc1cccc(C2=NOC3C=CS(=O)(=O)C23)c1] | Phenyl substituent at meta position |
| D11 | 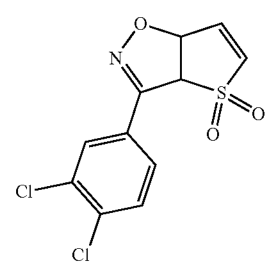 [SMILES: O=S1(=O)C=CC2ON=C(c3ccc(Cl)c(Cl)c3)C21] | Phenyl substituent at meta position and replacement of trifluoromethyl substituent at para position |
| D12 | 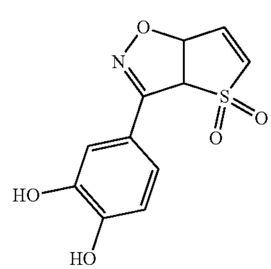 [SMILES: O=S1(=O)C=CC2ON=C(c3ccc(O)c(O)c3)C21] | Phenyl substituent at meta position and replacement of trifluoromethyl substituent at para position |

TABLE 2-continued

Compounds ("D-compounds") used for structure activity relationship studies, based on chemical modifications of the structure of Compound C17

| Compound Name | Compound Structure | Type of Primary Modification of Compound C17 |
|---|---|---|
| D13 | 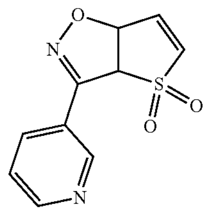 [SMILES: O=S1(=O)C=CC2ON=C(c3cccnc3)C21] | Replacement of phenyl with heteroaryl (pyridin-3-yl) |
| D14 | 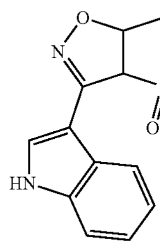 | Replacement of phenyl with heteroaryl (indolyl) |
| D15 | 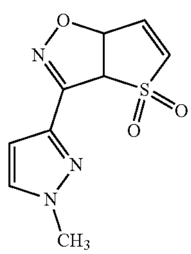 [SMILES: Cn1ccc(C2=NOC3C=CS(=O)(=O)C23)n1] | Replacement of phenyl with heteroaryl (N-methyl-pyrazol-3-yl) |
| D16 | 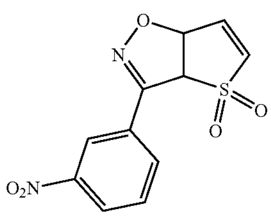 [SMILES: O=[N+]([O-])c1cccc(C2=NOC3C=CS(=O)(=O)C23)c1] | Phenyl substituent at meta position |
| D17 | 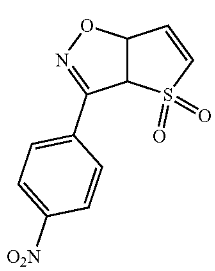 [SMILES: O=[N+]([O-])c1ccc(C2=NOC3C=CS(=O)(=O)C23)cc1] | Replacement of trifluoromethyl substituent at para position of phenyl |

A variety of electron withdrawal groups (EGW, σ>0) and electron donating groups (EDG, σ<0) of different sizes and hydrophobicity were included as substituents on the phenyl, in order to test the properties required for the activity and binding of the compound. The electron withdrawing or electron donating properties of exemplary substituents at the para- and meta-positions of phenyl, as well as parameters characterizing their size and hydrophobicity, are summarized in Table 3 below (data from Hansch & Leo (1979), *Substituent Constants for Correlation Analysis in Chemistry and Biology* (Wiley, New York) pp vii, p. 339).

TABLE 3

Examples of electron withdrawing groups (EWG, σ > 0) and electron donating groups (EDG, σ < 0) of varied sizes ($σ_V$) and hydrophobicity (π) as substituents in a benzene moiety (values for exemplary substituents in compounds of Table 2 are in bold).

| Group | $σ$meta (Hammet constant) | $σ$para (Hammet constant) | συ (Charton's υ (size) values) | π (hydrophobicity parameter) |
|---|---|---|---|---|
| —H | 0.00 | 0.00 | 0.00 | 0.00 |
| —CF$_3$ | 0.43 | 0.54 | 0.91 | 0.88 |
| —CH$_3$ | −0.07 | −0.17 | 0.52 | 0.56 |
| —F | 0.34 | 0.06 | 0.27 | 0.14 |
| —Cl | 0.37 | 0.23 | 0.55 | 0.71 |
| —OH | 0.12 | −0.37 | 0.32 | −0.67 |
| —OCH$_3$ | 0.12 | −0.27 | 0.36 | −0.02 |
| —OCH$_2$CH$_3$ | 0.10 | −0.24 | 0.48 | 0.38 |
| —NO$_2$ | 0.71 | 0.78 | 1.39 | −0.28 |

As shown in FIG. 13, most of the tested D-compounds show potent anti-viability activity (at a concentration of 10 μM), except for Compounds D7, D13 and D15, which each comprise a pyridine or pyrazole ring instead of a benzene ring.

As further shown therein, Compound D13 exhibited higher activity than did Compound D7, which is consistent with above-discussed results indicating that ortho-substituents in the benzene ring reduce the activity of the compound.

Furthermore, the results confirm that converting the ester bond of Compound Z2 to an isoxazole-type ring (e.g., as in Compound C17) results in significantly enhanced potency.

The compounds were then screened at a lower concentration of 1 μM, in order to identify the most active anti-proliferative compounds.

As shown in FIG. 14, Compounds D3, D11 and D14 presented particularly high anti-proliferative activity on both tested melanoma cell lines, reducing viability by up to 90% at a low concentration of 1 μM.

Notably, both Compounds D3 and D11 have two Cl substituents in the benzene ring, which are moderate electron-withdrawal groups. Furthermore, Compound D14 comprises an indole moiety instead of a benzene ring, which suggests further possible modifications (e.g., using Compound D14 as a lead compound).

A dose-response analysis (IC$_{50}$ assay) was then performed for the most active compounds (Compounds D3, D11 and D14) in order to assess their effect in eight cancer cells lines.

As shown in FIG. 15A, Compounds D3, D11 and D14 each exhibited significantly more potency than Compound C17 in reducing cell viability in six of the eight tested cell lines, and Compounds D3 and D11 showed slightly more potency than Compound D14 in seven of the eight cell lines.

As shown in FIG. 15B, Compounds D3 and D11 exhibited IC$_{50}$ values in the melanoma cells in a range of 40-250 nM, as compared to 400-1300 nM for Compound C17, indicating a 5-fold to 14-fold increase in potency relative to Compound C17 (depending on the cell type). As further shown therein, Compound D14 also presented significantly lower IC50 values compared to Compound C17, although it seemed be less selective since it did not affect cell viability of different cell types in the same manner as did Compounds D3 and D11.

As shown in FIG. 15C, at low concentrations of 120-370 nM, Compounds D3 and D11 have a similar effect on cell viability as does 10 μM EPE peptide, and exhibit considerably enhanced activity relative to Compounds C17 and D14 at such low concentrations.

As Compounds D3 and D11 are small molecular weight molecules, the obtained selectivity and potency are rather remarkable.

In addition, as shown in FIGS. 15B and 15C, Compounds C17 and D14 significantly decreased viability of PC3 cells, in which EPE peptide had only a very modest effect, whereas Compounds D3 and D11 did not.

As further shown in FIGS. 15A-15C, the potency of Compound C17 in LOX-IMVI melanoma cells is exceptionally low ($IC_{50}$ of about 20 nM), suggesting that the effect of Compound C17 in this cell line is via a non-specific mechanism.

The above results indicate that Compounds D3 and D11 are more selective than Compounds C17 and D14 in inhibiting ERK1/2 nuclear translocation.

Whether such the selectivity of Compounds D3 and D11 relative to Compound D14 is advantageous or disadvantageous may depend on the sensitivity of a given cell type to ERK1/2 nuclear translocation inhibition and/or to an additional mechanism exhibited by Compound D14.

Without being bound by any particular theory, it is believed that the lack of effect of the EPE peptide on the BRAF melanoma cells A2058 may be due to factors that result in less availability of the EPE peptide inside the cell, and does not indicate that blocking nuclear translocation of ERK1/2 has no effect in this line, especially as several other BRAF melanomas were very sensitive to the EPE peptide. It is further believed that the strong effect of Compounds D3 and D11 in reducing the viability of A2058 cells is associated with inhibition of ERK1/2 nuclear translocation, and may be due to improved availability and/or lack of degradation of the compounds inside the cell (relative to EPE peptide).

In order to confirm that the mechanism of action of Compounds D3, D11 and D14 is via inhibition of ERK1/2 nuclear translocation, their effects on nuclear translocation were assessed by fluorescent microscopy, according to procedures described hereinabove.

As shown in FIG. 16, Compounds D3, D11 and D14 exhibit convincing activity as inhibitors of ERK1/2 nuclear translocation, with Compound D3 appearing to be the most potent of the three tested compounds.

In summary, the above results indicate that substitution of an aromatic moiety such as in Compound C17 by moderately electron-withdrawing groups such as chloro affects the electronic properties of the benzene ring in a manner which facilitates a better interaction between the compound and the insert domain of ERK1/2. As a result, enhanced potency and selectivity of inhibitors was obtained.

Example 8

Further Studies of Structure-Activity Relationship of Sulfolene Ring

Further SAR analysis of compounds described hereinabove is performed based on modification of the phenyl group of Compound C17 (e.g., as depicted in FIG. 17) at one or both ortho-positions thereof.

Compounds comprising an ortho-substituted phenyl group (or aromatic analog thereof) are prepared using a general chemical synthetic route such as described in Example 7 and Scheme 1 hereinabove, wherein the N-hydroxybenzimidoyl chloride precursor (or analog thereof) comprises an ortho-substituted phenyl group (or analog thereof).

The activity of the obtained compounds is evaluated according to procedures described hereinabove. The effect of substituents at the ortho-position on activity is determined, so as to identify compounds with enhanced activity.

Example 9

Further Studies of Structure-Activity Relationship of Sulfolene Ring

Further SAR analysis of compounds described hereinabove is performed based on modification of the sulfolene ring of compounds described in Example 7 (e.g., as depicted in FIG. 17).

Compounds comprising a substituted or non-substituted sulfolane ring (instead of a sulfolene ring) and any of a variety of substituted or non-substituted aryl groups are prepared using a general chemical synthetic route based on a one step 1,3-cycloaddition reaction, as depicted in Scheme 2:

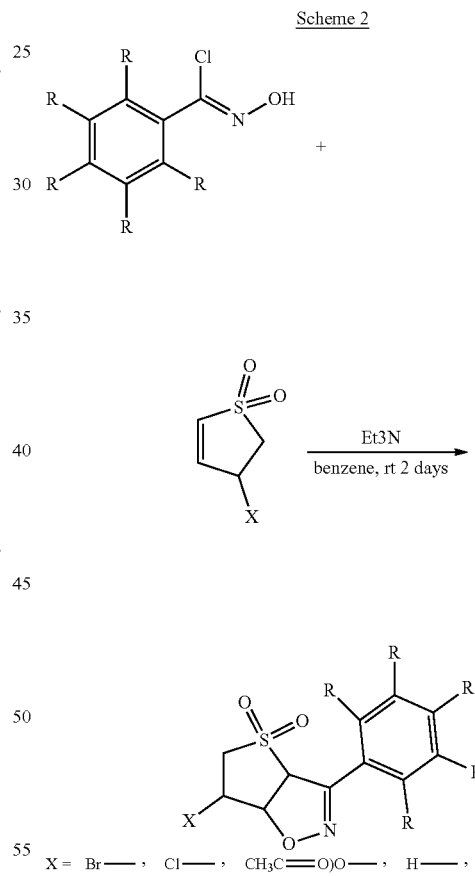

2-Sulfolene which is non-substituted or substituted at the 4-position (optionally by chlorine, bromine or acetoxy) is reacted with an equimolar amount of an N-hydroxybenzimidoyl chloride, or an analog thereof wherein the phenyl moiety is replaced by a different aromatic moiety (not shown in Scheme 2 for the sake of simplicity), for two days at room temperature in benzene and triethylamine. The reaction is regioselective (99% regioisomer of interest), and the product is purified by crystallization with ethanol. The N-hydroxybenzimidoyl chloride or an analog thereof is optionally one such as used to prepare a compound described in Example 7 or 8 or in Table 2.

The activity of the obtained compounds is evaluated according to procedures described hereinabove. The effect of substituents at the 4-position of a sulfolane ring on activity, and the interplay between the type of substituents and type of aromatic moiety is determined, so as to identify compounds with enhanced activity.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A compound represented by Formula I*:

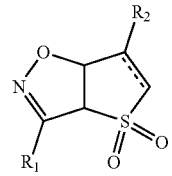

Formula I* wherein:
the dashed line represents a saturated or unsaturated bond;
$R_1$ is an aryl or heteroaryl, which is substituted by at least two electron withdrawing groups; and
$R_2$ is selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino,
wherein when $R_2$ is hydrogen, the dashed line represents an unsaturated bond,
and wherein $R_1$ is not 2,6-dichlorophenyl.

SEQUENCE LISTING

<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: short peptide sequence (EPE)
<220> FEATURE:
<221> NAME/KEY: MISC_FEATURE
<222> LOCATION: (1)..(1)
<223> OTHER INFORMATION: N-terminal conjugated to myristic acid

<400> SEQUENCE: 1

Gly Gln Leu Asn His Ile Leu Gly Ile Leu Gly Glu Pro Glu Gln Glu
1               5                   10                  15

Asp Leu

<210> SEQ ID NO 2
<211> LENGTH: 18
<212> TYPE: PRT
<213> ORGANISM: Artificial Sequence
<220> FEATURE:
<223> OTHER INFORMATION: Scramble (Scr) peptide amino acid sequence
      (used as a control peptide)
<220> FEATURE:
<221> NAME/KEY: MISC_FEATURE
<222> LOCATION: (1)..(1)
<223> OTHER INFORMATION: may be N-terminal conjugated to myristic acid

<400> SEQUENCE: 2

Gly Asn Ile Leu Ser Gln Glu Leu Pro His Ser Gly Asp Leu Gln Ile
1               5                   10                  15

Gly Leu

2. The compound of claim 1, wherein the dashed line represents an unsaturated bond.

3. The compound of claim 2, wherein $R_2$ is hydrogen.

4. The compound of claim 1, wherein $R_2$ is selected from the group consisting of hydrogen, halo and O-carboxy.

5. The compound of claim 1, wherein $R_1$ is a substituted aryl or a substituted indolyl.

6. The compound of claim 1, wherein said aryl or heteroaryl is substituted by two electron withdrawing groups.

7. The compound of claim 6, wherein each of said electron withdrawing groups is halo.

8. The compound according to claim 1, wherein $R_1$ is a substituted phenyl.

\* \* \* \* \*